(12) United States Patent
Larkin

(10) Patent No.: US 8,118,738 B2
(45) Date of Patent: Feb. 21, 2012

(54) VAGINAL SPECULUM INCLUDING COLLAPSIBLE AND EXPANDABLE FRAME

(76) Inventor: Daniel Larkin, St. Paul, MN (US)

( * ) Notice: Subject to any disclaimer, the term of this patent is extended or adjusted under 35 U.S.C. 154(b) by 1140 days.

(21) Appl. No.: 11/899,522

(22) Filed: Sep. 6, 2007

(65) Prior Publication Data

US 2009/0069634 A1    Mar. 12, 2009

(51) Int. Cl.
*A61B 1/32* (2006.01)
(52) U.S. Cl. ......................................................... 600/222
(58) Field of Classification Search .................. 600/206, 600/220–222, 233
See application file for complete search history.

(56) References Cited

U.S. PATENT DOCUMENTS

| | | | |
|---|---|---|---|
| 52,014 A | 1/1866 | Bartlett | |
| 208,227 A | 9/1878 | Dorr | |
| 367,248 A * | 7/1887 | Smith | 600/222 |
| 2,053,868 A * | 9/1936 | Grosso | 600/233 |
| 2,579,849 A | 12/1951 | Newmann | |
| 3,841,317 A | 10/1974 | Awais | |
| 4,807,600 A | 2/1989 | Hayes | |
| 4,994,070 A | 2/1991 | Waters | |
| 5,743,852 A | 4/1998 | Johnson | |
| 6,024,696 A * | 2/2000 | Hoftman et al. | 600/224 |
| 6,036,638 A | 3/2000 | Nwawka | |
| 6,379,299 B1 | 4/2002 | Borodulin et al. | |
| 6,416,467 B1 | 7/2002 | McMillin et al. | |
| 6,432,048 B1 | 8/2002 | Francois | |
| 6,740,031 B2 | 5/2004 | Davidson et al. | |
| 6,749,563 B2 | 6/2004 | Stihl | |
| 6,869,398 B2 | 3/2005 | Obenchain et al. | |
| 6,902,530 B1 | 6/2005 | Pianka | |
| 7,060,029 B1 | 6/2006 | Hajianpour | |
| 7,063,664 B2 | 6/2006 | Mohajer | |
| 7,081,090 B2 | 7/2006 | Strong et al. | |
| 7,229,408 B2 * | 6/2007 | Douglas et al. | 600/214 |
| 2003/0069477 A1 | 4/2003 | Raisman et al. | |
| 2003/0191371 A1 | 10/2003 | Smith et al. | |
| 2006/0074278 A1 | 4/2006 | Petit et al. | |
| 2006/0195017 A1 | 8/2006 | Shluzas et al. | |

* cited by examiner

*Primary Examiner* — Nicholas Woodall
(74) *Attorney, Agent, or Firm* — Dicke, Billig & Czaja, PLLC

(57) ABSTRACT

A vaginal speculum includes a frame and a first handle assembly pivotally mounted to the frame. The frame defines an opening between a first blade that is attachable to the frame and a second blade that is attachable to the frame opposite of the first blade, and a hinge assembly configured to flex the frame to selectively change a size of the opening. The first handle assembly includes a lever portion and a blade portion coupled to the lever portion. The blades have a proximal end attachable to the blade portion and a distal end portion spaced from the proximal end. When in a first collapsed insertion state, the hinge assembly collapses the frame and the first blade contacts the second blade. When in a second deployed state the hinge assembly expands the frame and the first blade is spaced apart from the second blade.

16 Claims, 21 Drawing Sheets

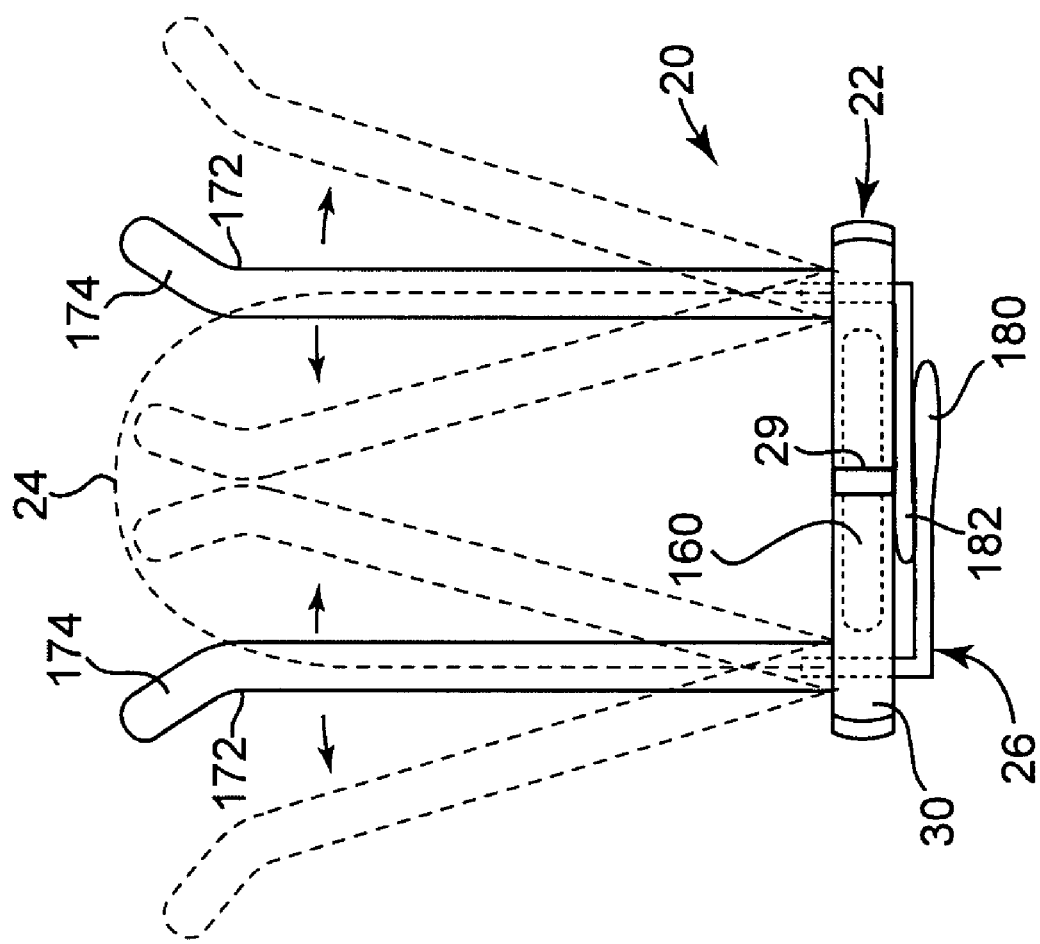

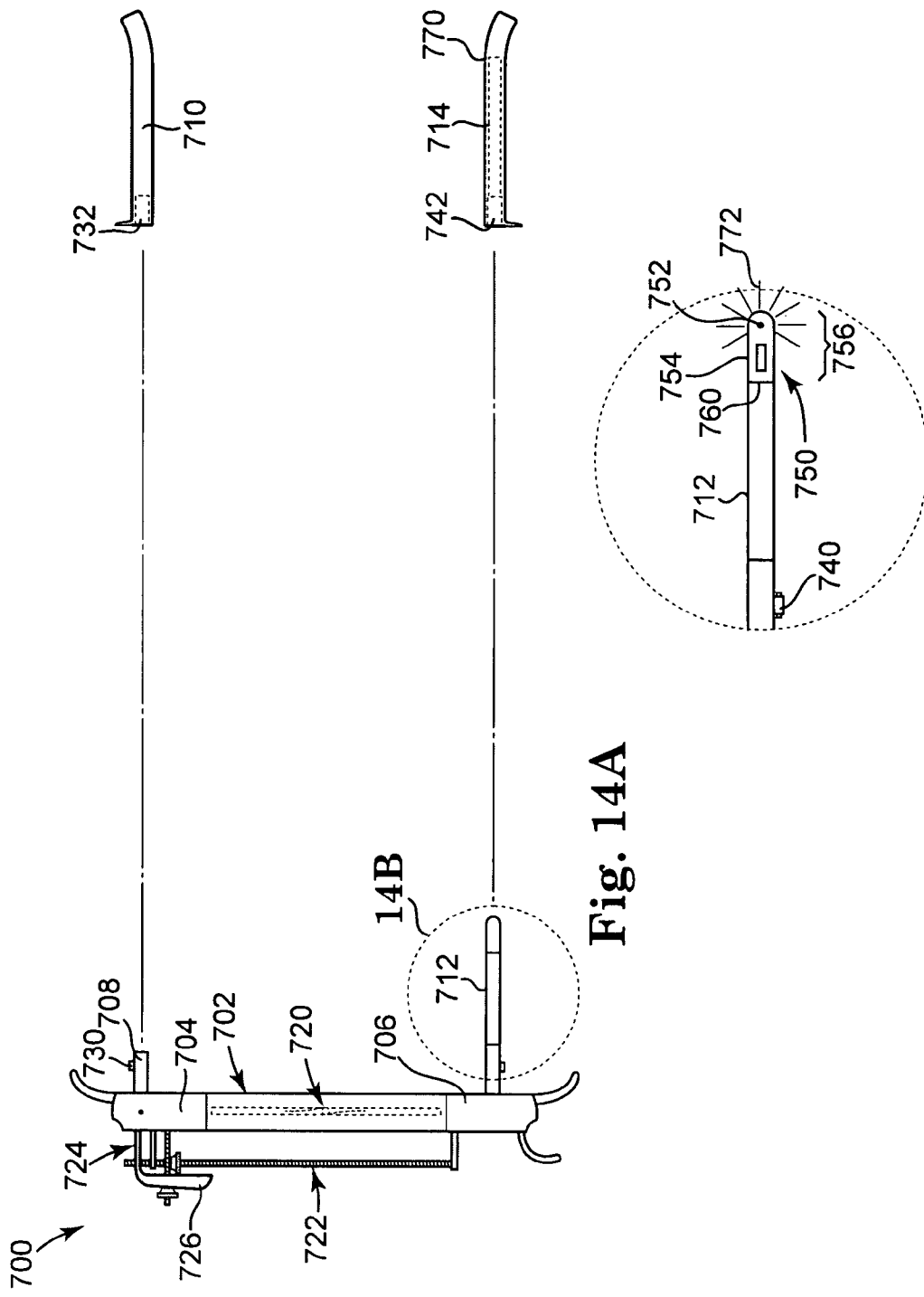

VAGINAL SPECULUM INCLUDING COLLAPSIBLE AND EXPANDABLE FRAME

BACKGROUND

Gynecological examinations have become established as well-care procedures that assist in the early detection of cervical pre-cancerous and cancerous growths. In general, a physician employs a speculum or similar device to expand and support the vaginal vault during the gynecological exam, which enables an unobstructed view of at least the exo-cervical wall.

FIG. 1 is a perspective view of a known speculum as disclosed in Hayes, U.S. Pat. No. 4,807,600. Speculum 2 is a rigid device that includes a handle 3 and an arm 4 coupled to the handle 3 about a hinge 5. A first blade 6 is integrally formed with handle 3 and a second blade 7 is integrally formed with arm 4. In the orientation shown in FIG. 1, first blade 6 is a lower blade of the speculum and second blade 7 is an upper blade. Each of blades 6, 7 include an inner surface 8 and an outer surface 9, where the outer surfaces 9 are those surfaces oriented to contact tissue of the patient. Movement of a thumb piece 10 results in moving upper blade 7 relative to lower blade 6 about hinge 5. A locking device 11 is provided to secure thumb piece 10 in position to maintain a desired position of blades 6, 7 during the gynecological exam.

For ease of description, operation of prior art speculums in general is illustrated with specific reference to the speculum of Hayes. However, other speculum configurations are known, but each generally includes a handle coupled to a rigid lower blade and a rigid upper blade. Speculum 2 is commonly provided in stainless steel for easy cleaning, although other rigid speculums are formed of plastic materials. During use, blades 6, 7 are brought together and inserted into the vaginal introitus. Thumb piece 10 is depressed to separate upper blade 7 from lower blade 6, thus expanding the walls of the vaginal vault. Locking device 11 is engaged to secure blades 6, 7 in their desired position. In this manner, the physician is able to visualize a portion of the cervix and have access to the endo-cervical canal for examination and/or the removal of samples/cells.

Although generally effective, operation of prior art speculums can undesirably apply pressure along the anterior midline of the pubic symphysis and the apposed internal vaginal walls. In particular, when the blades 6, 7 are parted, an upward movement of a proximal portion 12 of upper blade 7 can cause tissue discomfort during the examination procedure, especially in the sensitive region anterior to the pubic symphysis. In addition, even after blades 6, 7 are secured in their desired position, the weight of handle 3, arm 4, and thumb piece 10 (located outside the vaginal introitus opposite of blades 6, 7) conspire to cause blades 6, 7 to slide out of the desired position, thus displacing speculum 2 and requiring repositioning by the physician often increasing discomfort to the patient.

Improved speculums that are more comfortable will encourage patients to regularly schedule and follow through with these useful gynecological exams.

SUMMARY

One embodiment provides a vaginal speculum including a frame and a first handle assembly pivotally mounted to the frame. The frame defines a proximal side, a distal side, an opening within the frame between a first blade that is attachable to the frame and a second blade that is attachable to the frame opposite of the first blade, and a hinge assembly configured to flex the frame to selectively change a size of the opening. The first handle assembly includes a lever portion and a blade portion coupled to the lever portion. The lever portion extends from the proximal side of the frame and the blade portion extends from the distal side of the frame. Each of the opposing first and second blades has a proximal end configured for attachment to the blade portion of the handle assembly and a distal end portion spaced from the proximal end. When in a first collapsed insertion state, the hinge assembly collapses the frame and the first blade contacts the second blade. When in a second deployed state the hinge assembly expands the frame and the first blade is spaced apart from the second blade.

Another embodiment provides a vaginal speculum assembly including a frame, speculum blades attachable to the frame, and a lateral dilator insertable into the frame. The frame includes a first segment including a first end and a separate second end, a second segment including a first end and a separate second end, a first hinge assembly coupled between the first ends of the first and second segments, and a second hinge assembly coupled between the second ends of the first and second segments to form a frame periphery defining a proximal side opposite a distal side and an opening within the frame periphery. The speculum blades include a first speculum blade attachable to the first segment and a second speculum blade attachable to the second segment. Each of the first and second speculum blades has a proximal end attachable to the frame periphery and a distal end portion spaced from the proximal end. The lateral dilator is configured for insertion through the opening defined by the frame periphery and includes first and second opposed lateral blades. The hinge assemblies configure the first and second segments of the frame to collapse together to minimize the opening for insertion of the speculum blades into a vaginal introitus and configure the first and second segments of the frame to expand apart to maximize the opening to receive the lateral dilator.

Another embodiment provides a vaginal speculum configured to illuminate a vaginal vault during a gynecological procedure. The vaginal speculum includes a frame and first and second blades attachable to the frame. The frame includes a first segment and a first blade support coupled to the first segment, a second segment and a second blade support coupled to the second segment, where the frame defines an opening between the first and second segments. The first blade is attachable to the first blade support, and the second blade is attachable to the second blade support. One of the blades and blade supports comprises an illumination assembly configured to provide a source of light.

BRIEF DESCRIPTION OF THE DRAWINGS

Embodiments are better understood with reference to the following drawings. The elements of the drawings are not necessarily to scale relative to each other. Like reference numerals designate corresponding similar parts.

FIG. 7 is a top view of the speculum assembly shown in FIG. 2 when assembled.

FIG. 14A is an exploded side view of an illuminated speculum including an expandable/collapsible speculum frame and blades attachable to the speculum frame according to one embodiment.

FIG. 14B is a side view of an illuminated blade support of the illuminated speculum shown in FIG. 14A.

DETAILED DESCRIPTION

Figure 1:
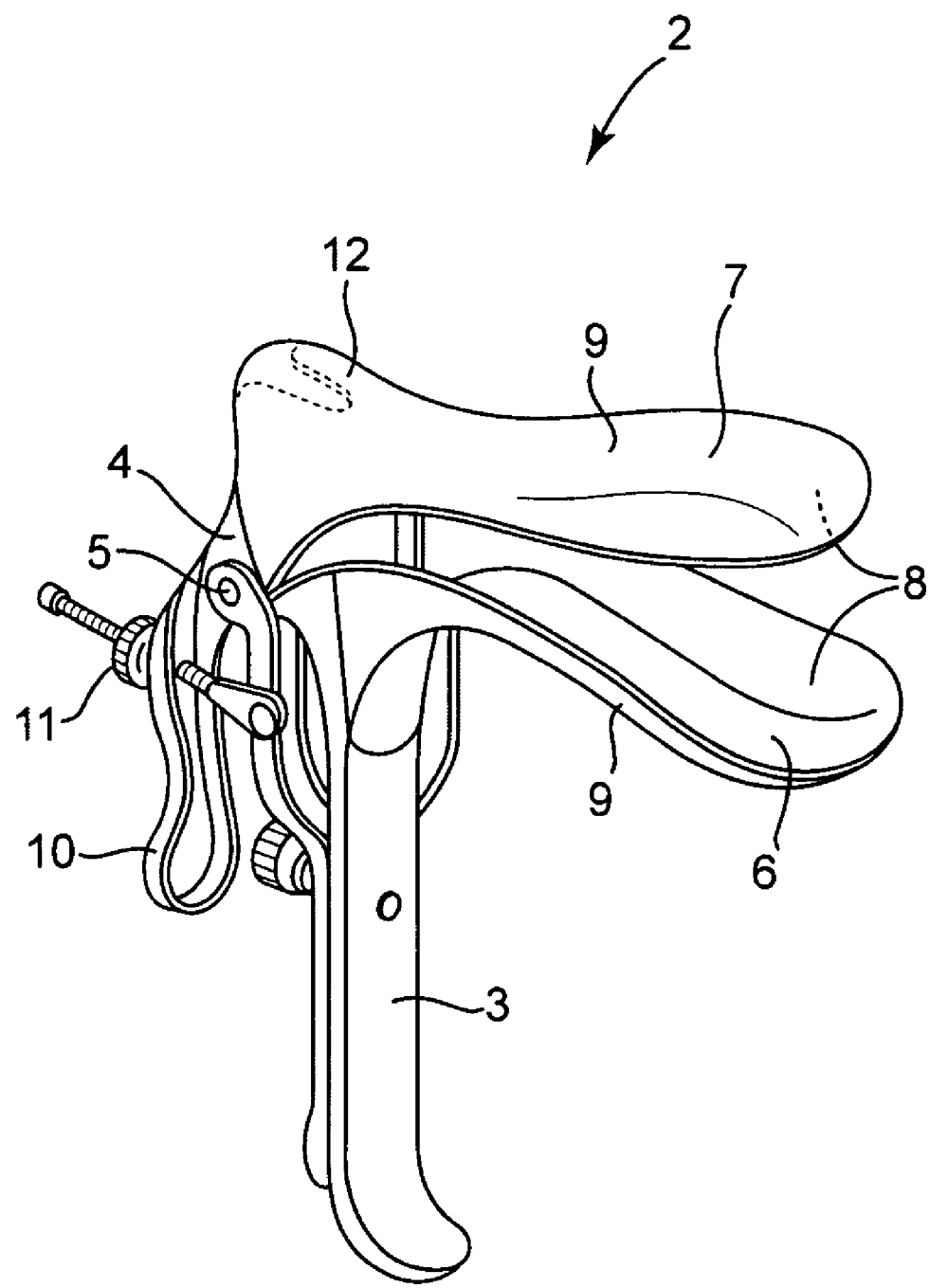
FIG. 1 is a perspective view of a representative prior art speculum including a handle and an upper blade movable relative to a lower blade.

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of the embodiments can be positioned in a number of different orientations, the directional terminology is used for purposes of illustration only and is in no way limiting. As employed in this application, the singular forms "a," "an," and "the" include the singular and the plural referents unless the context clearly dictates otherwise. Thus, for example, "a material" includes the specific material and other materials.

It is to be understood that other embodiments may be utilized and structural or logical changes may be made without departing from the scope of the present invention. The following detailed description, therefore, is not to be taken in a limiting sense, and the scope of the invention is defined by the claims.

Embodiments described below provide an expandable/collapsible "weight forward" vaginal speculum. As employed herein, the term "weight forward" means a vaginal speculum having a weight distribution that is configured to be heavier on the side of the speculum frame to which blades are attached. In other words, the portion of the vaginal speculum frame including the blades is heavier than the portion of the vaginal speculum frame including a handle assembly. The speculum assembly includes a collapsible frame having a first collapsed insertion state and a second expanded deployed state. The speculum assembly includes a hinge assembly that expands/collapses the frame and speculum blades that are configured to collapse together to enable comfortable insertion into the vaginal introitus, and expand apart to support walls of the vagina to enable access to the cervix during a gynecological procedure. When in the expanded state, the frame and the speculum blades are configured to minimize pressure along the anterior midline of the pubic symphysis, which thereby minimizes the discomfort often associated with gynecological procedures.

In one embodiment, the speculum assembly includes a speculum frame and blades attachable to the speculum frame, where the speculum frame is configured to flex/collapse for insertion into a vaginal introitus and configured to flex/expand to provide a visualization pathway to the cervix. The speculum frame includes a hinge assembly that enables the frame to flex and be collapsible and expandable to change a size/shape between collapsed and expanded states. In a collapsed insertion state, the speculum frame collapses along a hinge line to bring the speculum blades together in a manner suited for insertion into the vaginal introitus. Upon insertion, the frame is expanded to a second deployed state in which the speculum blades move apart to support top/bottom walls of the vagina and provide an opening suited for gynecological examination of the cervical region.

The speculum frame can be disposable or aseptically reusable. The speculum blades are attachable and detachable to the speculum frame and are preferably disposable. Other embodiments provide a lateral dilator insertable and connectible to the speculum frame that provides support to apposed side walls of the vagina.

Distal ends of the opposing first and second speculum blades selectively diverge to support walls of the vagina without increasing a distance between proximal ends of the speculum blades. In one embodiment, the proximal ends of the speculum blades minimally diverge as the distal ends of the speculum blades are diverged. In another embodiment, the proximal ends of the speculum blades do not diverge as the distal ends of the speculum blades are diverged. In this manner, an improved gynecological visualization channel can be formed without undesirably increasing pressure in the region of the anterior public symphysis of the patient. Embodiments described below provide a weight-forward speculum that is more comfortable to use and is configured to resist slipping out of the inserted position during the gynecological exam.

Figure 2:
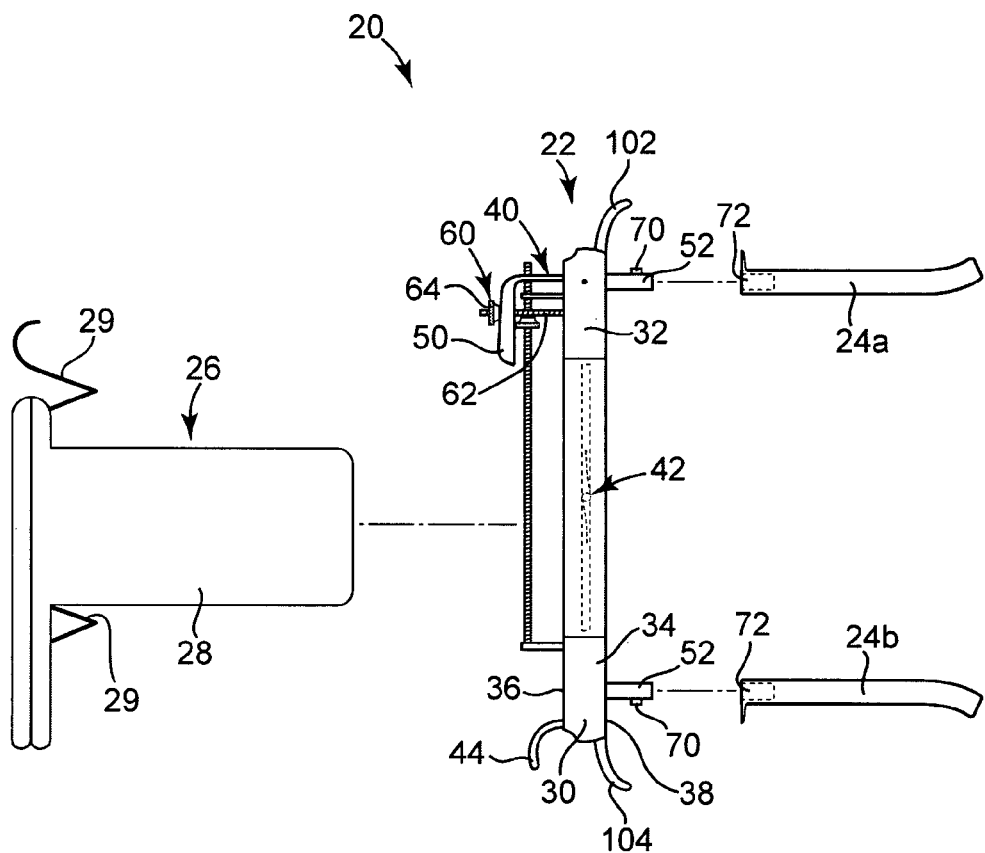
FIG. 2 is an exploded side view of a speculum assembly including a speculum frame, blades attachable to the speculum frame, and a lateral dilator insertable through the speculum frame according to one embodiment.

FIG. 2 is an exploded side view of a vaginal speculum assembly 20 according to one embodiment. Speculum assembly 20 includes a speculum 22, top/bottom speculum blades 24a, 24b, respectively, attachable to speculum 22, and a lateral dilator 26 insertable into speculum 22 that includes lateral blades 28 and a pair of attachment clips 29.

Speculum 22 generally includes a frame 30 including a first segment 32 and a second segment 34 that combine to define a proximal side 36 and a distal side 38, a handle assembly 40 coupled to frame 30, a hinge assembly 42 coupled between first segment 32 and second segment 34, and a trigger 44. Frame 30 is configured to collapse (i.e., configured to enable first segment 32 to move/fold or otherwise advance toward second segment 34) to provide comfortable insertion of speculum blades 24a, 24b during initiation of a gynecological procedure and thereafter expand to provide viewing access to the vaginal vault. Trigger 44 provides a grasping point along second segment 34 that is suited for gripping with a finger or thumb, which enables a clinician to collapse frame 30. In one embodiment, a flexible housing portion of frame 30 is integrally formed about hinge assembly 42 to minimize the risk of pinching the patient's skin and in a manner that enables first segment 32 to move relative to second segment 34 about hinge assembly 42.

Handle assembly 40 generally includes a lever portion 50 coupled to frame 30 on proximal side 36, and a blade portion 52 coupled to frame 30 on distal side 38. In one embodiment, handle assembly 40 is pivotally mounted to frame 30 such that movement of lever portion 50 deflects blade portion 52 up/down relative to the orientation shown in FIG. 2. A handle retention mechanism 60 is provided to selectively retain blade portion 52 in a desired position. In one embodiment, handle retention mechanism 60 includes a guide 62 and a retainer 64 movable along guide 62 that is configured to selectively "lock" lever portion 50 and blade portion 52. For example, lever portion 50 is moved a selected distance to raise/lower blade portion 52 to a desired position, and retainer 64 is locked against lever portion 50 along guide 62 to selectively lock lever portion (and thus blade portion 52) in the desired position.

Hinge assembly 42 is coupled between first segment 32 and second segment 34 of frame 30 and is configured to enable frame 30 to flex in a manner that moves speculum blades 24a, 24b together/apart relative to each other. Hinge assembly 42 generally enables frame 30 to be flexible (i.e., collapsible/expandable) and can include a pair of opposing hinge assemblies 42a, 42b as described below.

In one embodiment, frame 30 optionally includes a first lip 102 and a second lip 104 that are configured to appose a patient during a gynecological procedure to ensure that sensitive skin areas are not unduly irrigated by instruments or manipulation of frame 30. In another embodiment, protective lips are instead provided on each of blades 24a, 24b.

Blades 24a 24b are configured to removably couple with blade portions 52 on distal side 38 of speculum 22. In one embodiment, blade portions 52 each provide a spring-loaded socket connector 70 configured to removably couple with a socket 72 formed in a proximal end of the corresponding blade 24a, 24b. Blades 24a, 24b are preferably disposable, single-use blades that are attachable to a reusable and aseptically cleanable frame 30. When blades 24a, 24b are attached to speculum 22, movement of lever portion 50 will displace distal end portions of blades 24a, 24b away from each other in a manner configured to expand the walls of the vaginal vault. Frame 30 and handle assembly 40 are configured to move distal end portions of blades 24a, 24b apart without increasing a distance between proximal ends of blades 24a, 24b, as described in detail below.

Figure 3:
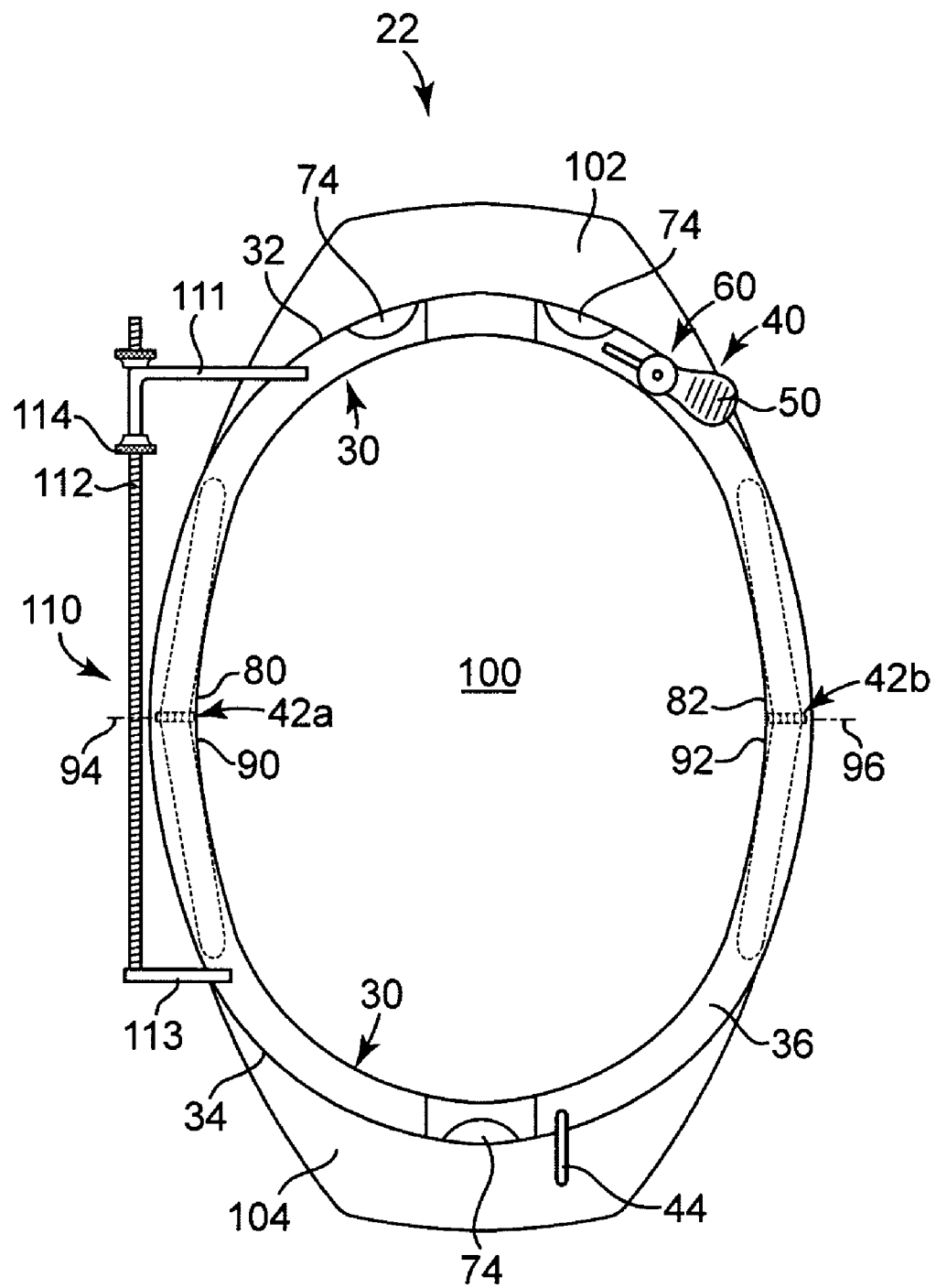
FIG. 3 is a plan view of a proximal side of the speculum frame shown in FIG. 2.

FIG. 3 is a plan view of proximal side 36 of speculum 22. In one embodiment, first segment 32 defines an arcuate segment extending between a first end 80 and a second end 82, and second segment 34 defines an arcuate segment extending between a first end 90 and a second end 92. In one embodiment, one or more depressions 74 are formed in one or both of segments 32, 34 to provide a grasping area for the clinician's fingers. A first hinge assembly 42a is coupled between respective first ends 80, 90 of first and second segments 32, 34 to define a first hinge line 94, and a second hinge assembly 42b is coupled between respective second ends 82, 92 of first and second segments 32, 34 to define a second hinge line 96. Arcuate segments 32, 34 combine to define an opening 100 within a periphery of frame 30. Frame 30 of speculum 22 flexes along hinge lines 94, 96 to change a size of opening 100.

In one embodiment, a first lip 102 is coupled to first segment 32, and a second lip 104 is coupled to second segment 34, where lips 102, 104 extend toward distal side 38 (as best illustrated in FIG. 2) of speculum 22. Lips 102, 104 are configured to appose a patient during a gynecological procedure to ensure that sensitive skin areas are not unduly irrigated by instruments or manipulation of frame 30.

Hinge assemblies 42a, 42b configure frame 30 to flex such that first segment 32 is collapsible toward second segment 34 to minimize opening 100 for insertion of blades 24a, 24b into the vaginal introitus during a gynecological procedure. After insertion, hinge assemblies 42a, 42b configure frame 30 to expand such that first section 32 moves away from second section 34 to maximize opening 100 for access to the vaginal vault and the cervical region.

In one embodiment, a frame retention mechanism 110 is coupled between sections 32, 34 of frame 30 to selectively maintain frame 30 in a desired expanded state. Frame retention mechanism 110 includes a first flange 111 coupled to first section 32 of frame 30 and a second flange 113 coupled to second section 34 of frame 30, a threaded guide 112 extending between flanges 111, 113, and lock nuts 114 coupled to and movable along guide 112. In one embodiment, guide 112 is fixed to second flange 113 and movable through a slot in first flange 111. In general, hinge assemblies 42a, 42b combine to move segments 32, 34 apart, and lock nuts 114 are provided to selectively limit an amount of separation between segments 32, 34. For example, when the desired opening 100 is established between first section 32 and second section 34, an upper one of the lock nuts 114 is threaded/moved down guide 112 to seat against flange 111 and selectively maintain a distance between first section 32 and second section 34. A lower one of the lock nuts 114 is provided to ensure that opening 100 is maintained during the procedure. Other forms of retention mechanisms are also acceptable. In one embodiment, frame retention mechanism 110 includes a ratchet rod having detents that are configured to ratchet relative to an engagement edge of the first flange 111. Frame 30 is formed of suitable materials configured to enable first and second sections 32, 34 to flex relative to hinge lines 94, 96. Examples of suitable materials for frame 30 include braided stainless steel that is configured to enclose and flex laterally relative to hinge assemblies 42a, 42b, a flexible frame 30 formed of a polymer or a polymer blend or a co-polymer, and a frame 30 having rigid sections 32, 34 that bend along hinge lines 94, 96 (such that lips 102, 104 bend in/out of the plane of the page in FIG. 3, for example). In one embodiment, first and second sections 32, 34 of frame 30 are molded from polymer such as a high density polyethylene and attached to hinge assemblies 42a, 42b. Other suitable materials for frame 30 are also acceptable.

Figures 4A, 4B:
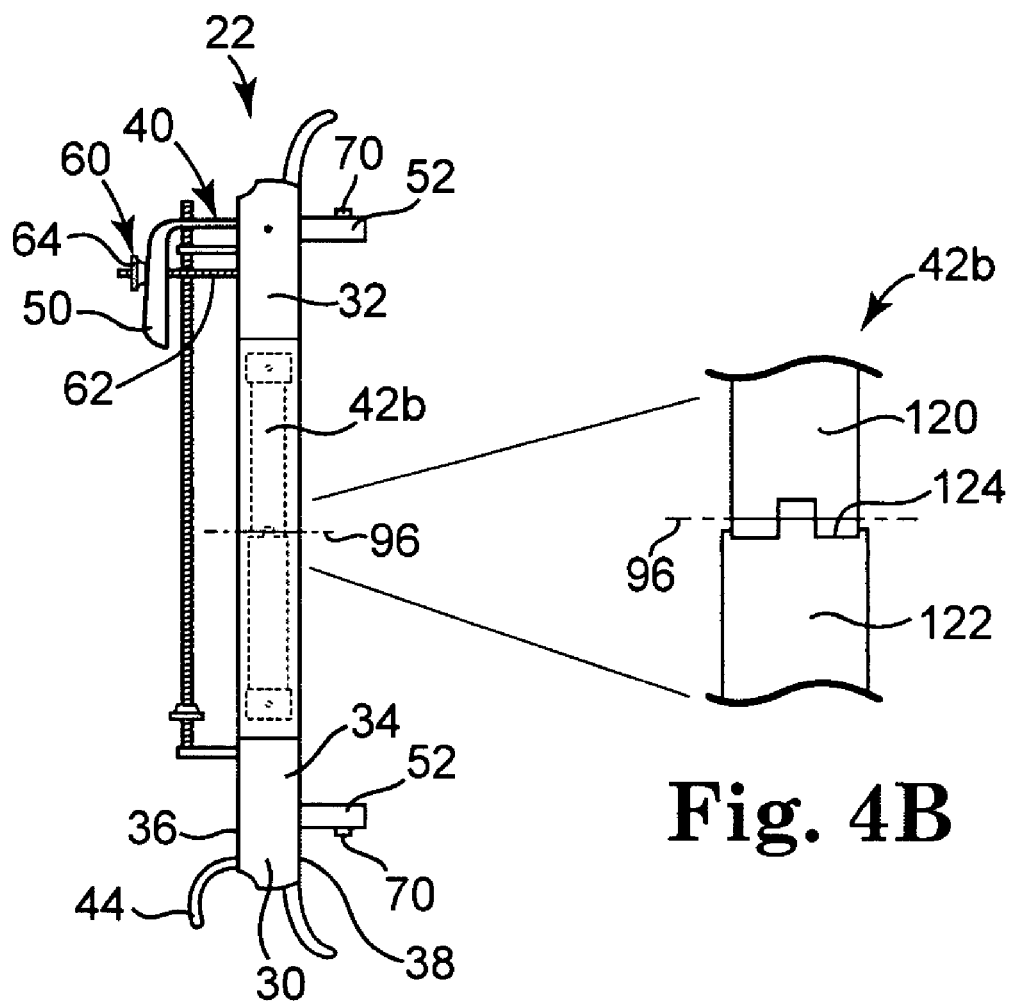
FIG. 4A is a side view of a speculum frame according to one embodiment.
FIG. 4B is an enlarged view of a hinge assembly of the speculum frame shown in FIG. 4A.

FIG. 4A is a side view of speculum 22 showing a relative location of hinge assembly 42b, and FIG. 4B is an enlarged view of hinge assembly 42b. In one embodiment, hinge assembly 42b includes a leaf spring mechanism having a first band 120 that is coupled to first section 32 of frame 30, a second band 122 that is coupled to second section 34 of frame 30, where second band 122 is movably coupled to first band 120 along a joint 124. In one embodiment, bands 120, 122 are metal bands that flex/deform and recover relative to joint 124. In one embodiment, joint 124 is a pinned coupling between bands 120, 122. When first section 32 is displaced and collapsed towards second section 34, hinge assembly 42b deforms along joint 124 and frame 30 flexes/flattens into an oval or substantially flat shape such that opening 100 (FIG. 3) is minimized.

During initial insertion of speculum 22, and with reference to FIG. 3, first and second sections 32, 34 of speculum 22 are collapsed together by the clinician using one or both hands. For example, speculum 22 is suited for grasping by one hand where fingers are aligned along first section 32 and the thumb is placed along second section 34, where the thumb and fingers brought together to compress speculum 22 into a flat (or substantially oval) shape.

Hinge assemblies 42a, 42b are configured to enable first section 32 to collapse toward second section 34, and are also configured to provide an expansion force to subsequently first section 32 away from second section 34 when speculum 22 is inserted into the vaginal introitus. To this end, hinge assemblies 42a, 42b are configured to have an appropriate spring constant k that enables an average clinician to compress speculum 22 in a one-handed manner, and yet have enough spring force to recover and expand speculum 22 after blades 24a, 24b are inserted into the vaginal introitus.

In one embodiment, hinge assemblies 42a, 42b are compressible and include a spring constant k of less than about 10.8 pounds per inch. This relatively low spring constant k is selected as being the lowest pinch force value for all subjects based on the average performance of all subjects (male and female, left and right handed) when tested in a tip pinch challenge employing a B&L pinch gauge, available from B&L Engineering, Tustin, Calif. (as reported in Grip and Pinch Strength: Normative Data for Adults, Mathiowetz et al., ARCH PHYS MED Rehabil 66: 69-72, 1985). For example, left handed female subjects applied a pinch force of about 10.8 pounds when challenged by the B&L pinch gauge. Thus, in one embodiment the spring constant k of hinge assembly 42 is selected to accommodate the pinch force that left handed female clinicians are able to apply to speculum 22.

In one embodiment, spring constant k for hinge assemblies 42a, 42b is selected to be slightly higher than the average subject pinch strength for all left handed female subjects (having the lowest pinch strength), such that a suitable spring constant k is between about 10-25 pounds per inch. In this manner, although the spring constant k is slightly higher than the mean pinch strength for the weakest clinicians, the spring constant for the force of the hinge assembly 42a, 42b is selected to provide a relatively larger recovery force, which is suited to optimally expand speculum 22 after being inserted the vaginal introitus.

Suitable springs for hinge assembly 42 include wound wire springs, clip springs, leaf springs, coiled springs, flat springs, and the like. In one embodiment, springs employed in hinge assemblies, 42a, 42b are plastic springs. In other embodiments, springs employed in the hinge assemblies 42a, 42b are metal springs. One suitable hinge assembly 42 includes a metal torsion spring available from Associated Spring, Hartford, Conn. Other suitable springs for hinge assembly 42 include coiled springs, compression springs, and/or conical springs available from MW Industries, Logansport, Ind.

Figure 5A:
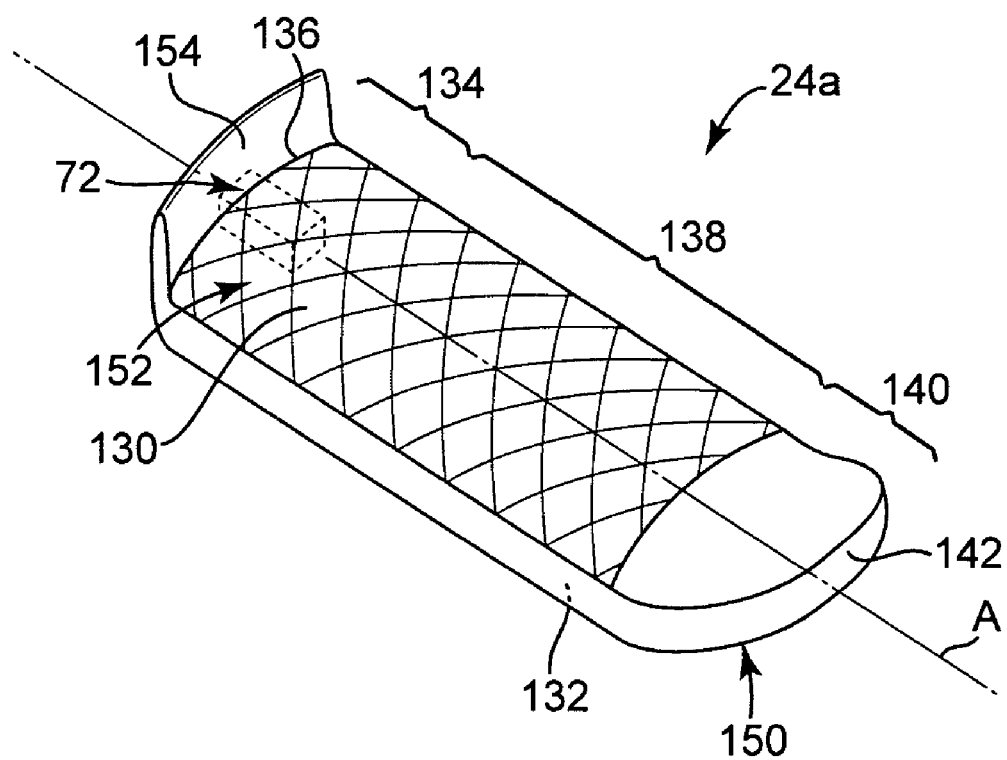
FIG. 5A is a perspective view of one of the speculum blades of the speculum assembly shown in FIG. 2.

FIG. 5A is a perspective view of speculum blade 24a shown in FIG. 2, where the second opposing blade 24b is substantially similar. Blade 24a includes an exterior surface 130 configured for patient contact opposite an interior surface 132, a proximal end portion 134 extending between a proximal end 136 and a central portion 138, and a distal end portion 140 extending between a distal end 142 and central portion 138. Socket 72 is formed in proximal end portion 134 and is sized to receive blade portion 52 (FIG. 2) of handle assembly 40. In one embodiment, blade 24a extends along a longitudinal central axis A and distal end portion 140 includes a retention lip 150 that curves away from longitudinal axis A in an upward direction (relative to the orientation of FIG. 5A). Retention lip 150 is configured to support a portion of the vaginal vault in providing improved visualization of the cervix and adjacent vaginal walls during a gynecological procedure.

In one embodiment, blade 24a is configured for single use only and is disposable. In another embodiment, blade 24a is reusable and formed of a material suited for repeated use and cleaning, such as stainless steel, or includes a soft aseptically cleanable polymer such as silicone.

In one embodiment, exterior surface 130 defines a generally convex shape including pads 152 that are integrally formed to be soft, resilient, and flexible and configured to distribute pressure evenly across sensitive tissue when employed in a gynecological procedure. In another embodiment, blade 24a is a rigid blade formed to define socket 72 and receive a separate cover as described in co-pending U.S. utility patent application Ser. No. 11/728,755 entitled SPECULUM BLADE COVER, which is incorporated into this disclosure in its entirety. In one embodiment, blades 24a removably couple with blade portion 52 (FIG. 2) of handle assembly 40. In one embodiment, a lip 154 is provided along proximal end 136 to minimize the possibility of pinching the patient's skin between blade 24 and frame 30.

Figure 5B:
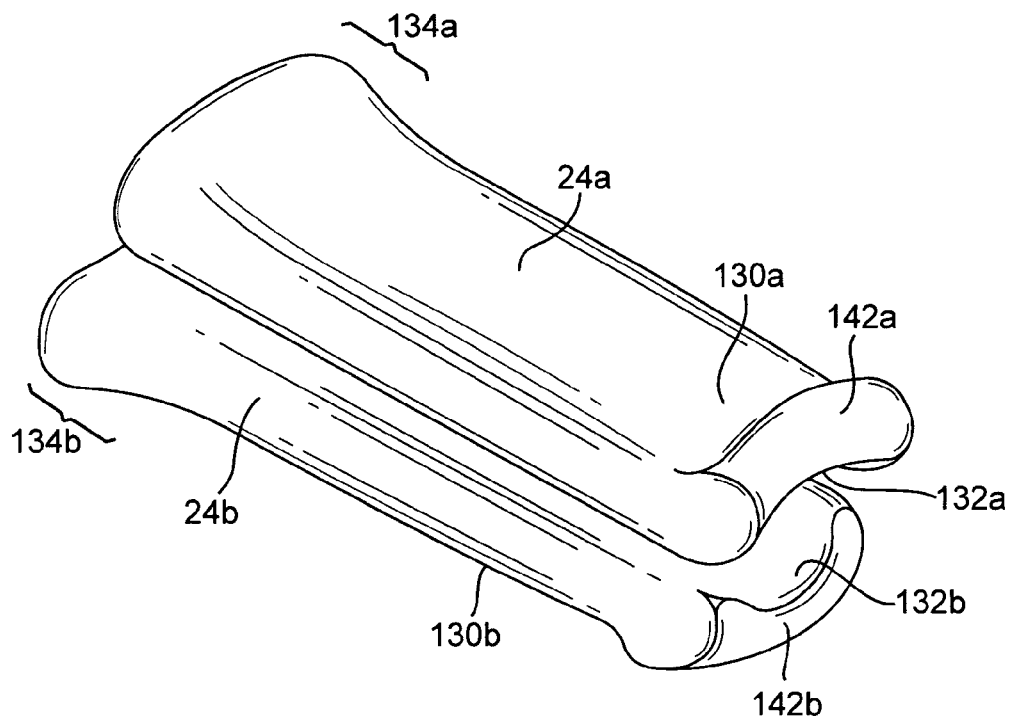
FIG. 5B is a perspective view of distal ends of the speculum blades when assembled to the speculum frame shown in FIG. 2.
Figure 5C:
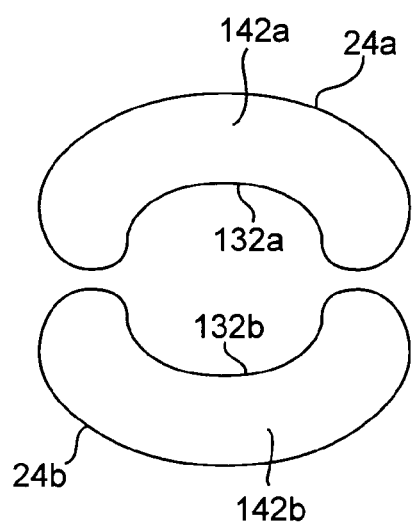
FIG. 5C is a front view of the distal ends of the speculum blades shown in FIG. 5B.

FIG. 5B is a perspective view of distal ends 142a, 142b of speculum blades 24a, 24b, respectively, as they would appear when assembled on speculum 22 (FIG. 2), and FIG. 5C is a front view of distal ends 142a, 142b. Distal ends 142a, 142b are configured to provide improved retention of blades 24a, 24b within the vaginal vault and a wider, unimpeded view of the cervical area. The exposed exterior surfaces 130a, 130b are convex and the interior surfaces 132a, 132b are curved to provide an opening between the apposed blades 24a, 24b, thus providing improved visual and physical access to the cervix. In one embodiment, proximal end portions 134a, 134b are smoothly curved to define another embodiment of a protective lip in which the lip is gently radiussed to prevent undesirable pinching of sensitive skin between speculum 22 and blades 24a, 24b.

Figure 6A:
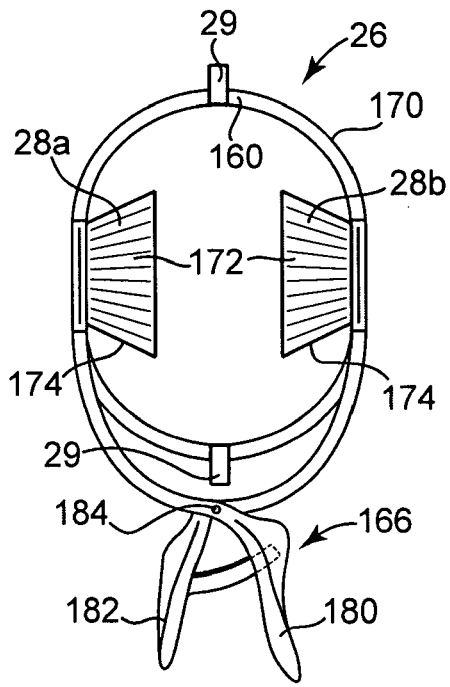
FIG. 6A is a plan view of a proximal side of the lateral dilator shown in FIG. 2 illustrating lateral blades of the dilator in an insertion orientation.
Figure 6B:
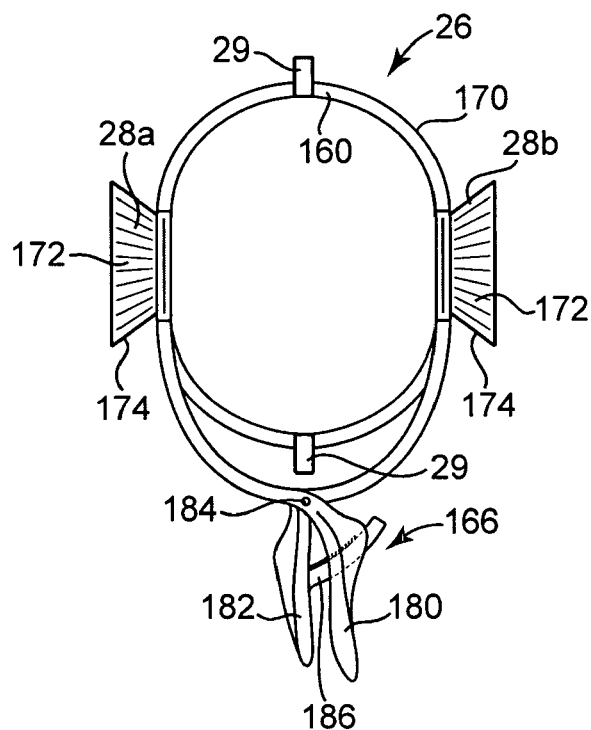
FIG. 6B is a plan view of the lateral dilator shown in FIG. 6A illustrating the lateral blades in a deployed orientation.

FIG. 6A is a plan view of a proximal side of lateral dilator 26 illustrating lateral blades 28a, 28b collapsed together in an insertion orientation, while FIG. 6B illustrates a similar view showing lateral blades 28a, 28b expanded in a deployed orientation.

Lateral dilator 26 includes a collar 160, first and second opposed lateral blades 28a, 28b coupled to and extending from collar 160, and a dilator handle assembly 166 pivotally mounted to collar 160. Operation of dilator handle assembly 166 moves lateral blades 28a, 28b laterally left/right relative to collar 160. Lateral dilator 26 is preferably reusable and is formed of a material suited for aseptic cleaning between procedures, such as stainless steel. In one embodiment, lateral dilator 26 is injection molded from a suitable polymer such as polyethylene, polypropylene, polyester, or other polymers.

In one embodiment, collar 160 includes a collar wall 170 that is configured to removably couple with frame 30 (FIG. 2) and be held in place by attachment clips 29. Mechanisms other than the leaf-spring form of clips 29 for coupling collar 160 to frame 30 are also acceptable, and include pins, snaps, etc. In one embodiment, collar 160 is a rigid collar and an outer peripheral edge of collar wall 170 is sized to snap-fit against an inner edge of frame 30 (FIG. 3). Other suitable forms of coupling collar 160 to frame 30 are also acceptable, such a pinning and/or clipping collar 160 to the proximal side 36 of frame 30.

Each of the lateral blades 28a, 28b define a rigid elongated lateral blade that extends from collar 160 by about 3-4 inches and includes a splayed section 172 adjacent a distal end portion 174. In one embodiment, dilator handle assembly 166 includes a first lever 180 coupled to first lateral blade 28a and a second lever 182 coupled to second lateral, blade 28b. First lever 180 and second lever 182 are coupled to collar 160 about a pivot point 184 such as a hinge pin. FIG. 6A illustrates dilator handle assembly 166 in an insertion position in which first and second levers 180, 182 are separated and distal end portions 172 of lateral blades 28a, 28b are closed together in an orientation suited for insertion of dilator 26 into opening 100 of frame 30 (FIG. 3).

FIG. 6B illustrates dilator handle assembly 166 in a deployed position in which first and second levers 180, 182 have been squeezed together to move distal end portions 172 of lateral blades 28a, 28b laterally apart and beyond the circumference defined by collar 160. Dilator 26 is illustrated apart from speculum 22 (FIG. 3) for clarity of illustration, but it is to be understood that dilator blades 28a, 28b are spread apart after first being inserted through opening 100 of frame 30 after speculum 22 has been inserted. After inserting dilator 26 into the opening 100 and securing attachment clips 29 to frame 30, squeezing first and second levers 180, 182 together moves blades 28a, 28b outward relative to collar 160 and rotates distal end portions 172 of lateral blades 28a, 28b out to their deployed position. In one embodiment, a ratcheting retention mechanism 186 extending between first and second levers 180, 182 is provided to selectively retain levers 180, 182 in a desired deployed position. In this manner, distal end portions 172 of lateral blades 28a, 28b can be selectively diverged to support lateral walls of the vaginal vault as speculum blades 24 (FIG. 2) support top/bottom walls of the vaginal vault.

FIG. 7 is a top view of the vaginal speculum assembly 20 shown in FIG. 2 as assembled. Lateral dilator 26 has been inserted into opening 100 and collar 160 has been coupled to frame 30. Speculum blades 24 are movable up and down (in and out of the paper as illustrated in FIG. 7), and lateral blades 28a, 28b are movable laterally (left and right as oriented in FIG. 7).

During a gynecological procedure, frame 30 is compressed to collapse opening 100 and bring speculum blades 24 together until blades 24 touch (or nearly touch). The speculum blades 24 attached to collapsed frame 30 are inserted into the vaginal introitus until lips 102, 104 protectively appose the patient. When compression force applied to the hinge assembly 42 is relieved by the physician releasing his/her grip on frame 30, frame 30 expands and speculum blades 24 move apart to support top/bottom walls of the vaginal vault. Speculum blades 24 may be further diverged, or optimally positioned according to physician preference, by movement of handle assembly 40 to suitably size opening 100 for the gynecological procedure.

After insertion of speculum 22, lateral blades 28a, 28b of dilator 26 are inserted into opening 100 and collar 160 is coupled to frame 30. Levers 180, 182 of handle assembly 166 (FIG. 6A) are squeezed and lateral blades 28a, 28b are diverged one apart from the other to support lateral walls of the vaginal vault. In one embodiment, the lateral blades 28a, 28b of dilator 26 are removable blades similar to blades 24a, 24b employed by speculum 22 (FIG. 2) and are configured to couple to blade portions on collar 160 that are similar to blade portion 52 of frame 30 (FIG. 2).

Frame 30 and handle assembly 40 are configured to diverge the distal end portions 140 (FIG. 5) of speculum blades 24 without increasing a distance between proximal ends 136 of blades 24. To this end, the pressure applied to the anterior midline of the pubic symphysis is minimized and the procedure is more comfortable for the patient. In a similar manner, distal end portions 174 of lateral blades 28a, 28b are configured to diverge apart without moving proximal ends of lateral blades beyond collar 160 or frame 30. Most of the weight of speculum 22 is distributed on the distal side 38 of frame 30 when speculum 22 is positioned as described above. That is to say, blades 24 and frame 30 contribute to a majority of the weight of speculum 22, such that speculum 22 provides a "weight forward" vaginal speculum. This weight forward orientation is unchanged when blades 28 of dilator 26 are inserted into frame 30.

Embodiments described herein provide an expandable/collapsible "weight forward" vaginal speculum assembly including a speculum frame and blades attachable to the speculum frame, where the speculum frame is configured to collapse for insertion into a vaginal introitus and configured to expand to provide a visualization pathway to the cervix. Other embodiments of a speculum frame configured to be collapsible and expandable to change states, apart from that embodiment described above, are also within the scope of this application and are described below.

Figure 8:
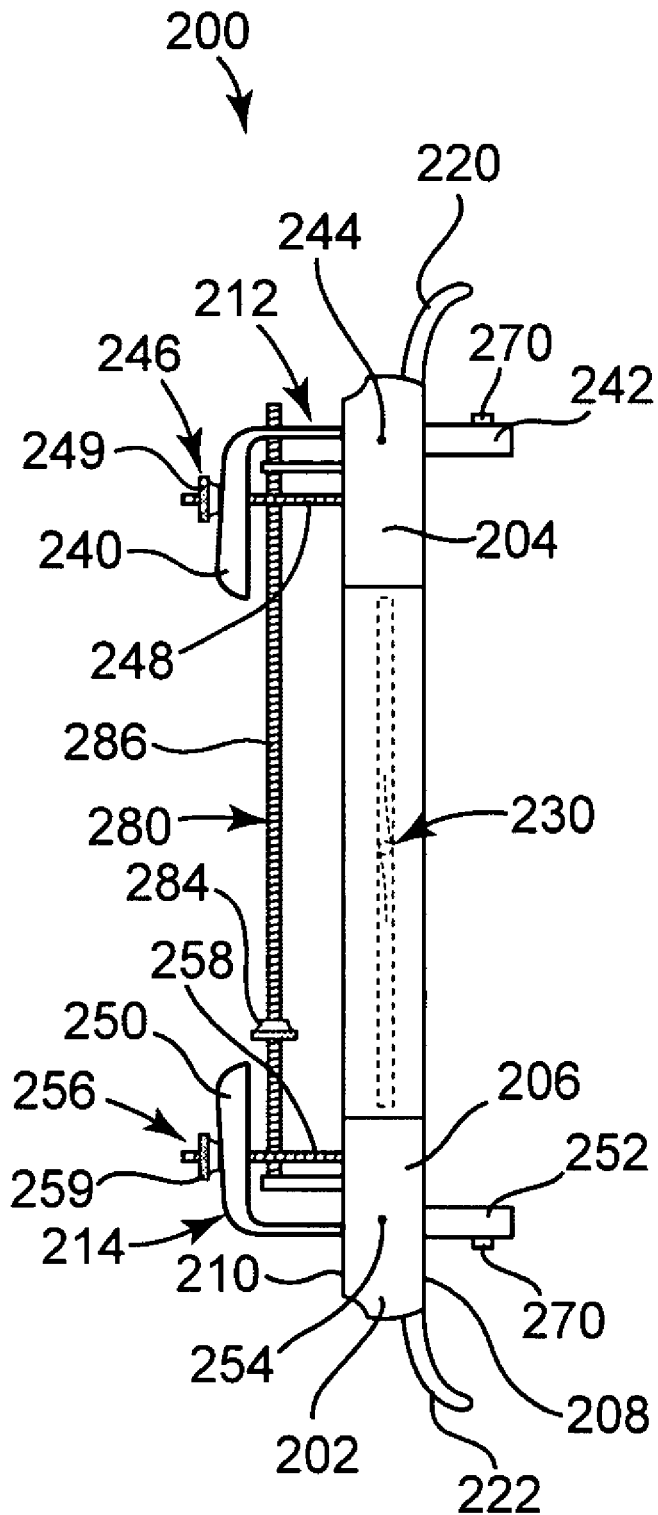
FIG. 8 is a side view of a speculum frame including a pair of handle assemblies according to another embodiment.

FIG. 8 is a side view of another embodiment of a vaginal speculum 200 including a pair of handle assemblies 212, 214 each suitable for coupling to one of the removable blades 24 (FIGS. 2 and 5). Speculum 200 includes a frame 202 having a first section 204, a second section 206 coupled to first section 204 to define a distal side 208 opposite a proximal side 210, a first handle assembly 212 coupled to first section 204, and a second handle assembly 214 coupled to second section 206.

In one embodiment, first section 204 is similar to first section 32 (FIGS. 2 and 3) and defines an arcuate section having a lip 220 extending from first section 204. Second section 206 is similar to second section 34 described above and includes a lip 222 extending from second section 206. Lips 220, 222 are configured to appose the patient and minimize the risk that sensitive skin is pinched or irritated during the gynecological procedure.

In one embodiment, first section 204 and second section 206 are coupled together by a pair of hinge assemblies 230 similar to the hinge assemblies 42 described above in FIGS. 2 through 4B to define an access opening (not shown). Hinge assembly 230 is configured to enable first section 204 to be collapsed toward second section 206 to compress speculum 200 to a size and shape that is suitably minimized for insertion of the speculum 200 into the vaginal introitus.

It is to be understood that speculum 200 is usefully employed with a pair of speculum blades, such as speculum blades 24 (FIG. 5). Speculum 200 is configured to be collapsed such that blades 24 are brought together to touch one another for insertion into the vaginal introitus. After insertion of the collapsed speculum 200, hinge assembly 230 expands first section 204 apart from second section 206 to provide a pathway to the patient's cervix. First handle assembly 212 is configured to move a first one of the blades 24, and second handle assembly 214 is configured to move a second one of the blades 24 independent of the first blade, to more optimally provide access to the cervix during the gynecological procedure.

In one embodiment, first handle assembly 212 includes a lever portion 240, a blade portion 242 coupled to lever portion 240, a pin 244 that pivotally mounts handle assembly 212 to first section 204, and a handle retention mechanism 246 configured to retain blade portion 242 in a selected deployed position.

In one embodiment, lever portion 240 defines an oblong lever suited for manipulation by a thumb or finger of a clinician. Lever portion 240 is mechanically coupled to blade portion 242 such that when lever portion 240 is moved, blade portion 242 moves up/down (relative to the orientation of FIG. 8) to move an attached speculum blade 24 up/down. Lever portion 240 is manipulated to position a distal end portion of speculum blade 24 to a desired location, and retention mechanism 246 is deployed to maintain speculum blade 24 in the desired position. Handle retention mechanism 246 includes a guide 248 fixed to and extending from first section 204 through a slot in lever portion 240, and a lock 249 configured to secure lever portion 240 relative to guide 248, in a manner similar to handle retention mechanism 60 (FIG. 2). It is believed that with experience, the clinician will become adept at adjusting and locking lever portion 240 in a one-handed manner.

Speculum 200 includes a second handle assembly 214 including a second lever portion 250, a second blade portion 252 coupled to lever portion 250, and a pin 254 that pivotally couples handle assembly 214 to second section 206 of speculum 200. In one embodiment, lever portion 250 extends away from proximal side 210 of frame 202 and blade portion 252 extends from distal side 208. In one embodiment, second handle assembly 214 includes a retention mechanism 256 configured to maintain a position of lever portion 250 relative to second section 206. For example, retention mechanism 256 is similar to retention mechanism 246 and includes a guide 258 extending from second section 206 through a slot in lever portion 250, and a lock 259 configured to selectively retain lever portion 250 relative to guide 258.

First handle assembly 212 and second handle assembly 214 are each configured to independently move a speculum blade 24 coupled to one of the blade portions 242, 252. Lever portion 250 is movable to position a distal end portion 140 of the first speculum blade 24 coupled to blade portion 242 to a desired location, and second lever portion 250 is movable to position the second speculum blade 24 in a desired position. Each of first blade portion 242 and second blade portion 252 include a spring loaded socket retainer 270 configured to removably couple with socket 72 (FIG. 2) formed in speculum blades 24.

In one embodiment, speculum 200 includes a frame retention mechanism 280 that is similar to frame retention mechanism 110 (FIG. 3), and likewise includes a nut 284 coupled to a guide 286 that combine to maintain a desired relative position between first section 204 and second section 206 when speculum 200 is in an inserted position. In general, frame 202, including blades 24, is collapsed to an insertion state in which first section 204 and second section 206 are brought together until blades 24 contact one another (or nearly contact one another), speculum 200 is inserted into the vaginal introitus, and hinge assembly 230 expands first section 204 away from second section 206. Frame retention mechanism 280 is employed to maintain a selected distance between first and second sections 204, 206; Handle assemblies 212, 214 are deflected to move a distal end portion of blades 24 apart to support and retract the vaginal walls. When a desired positioning of distal end portions of blades 24 is achieved, handle retention mechanisms 246, 256, respectively, are secured to hold blades 24 in position.

Figure 9A:
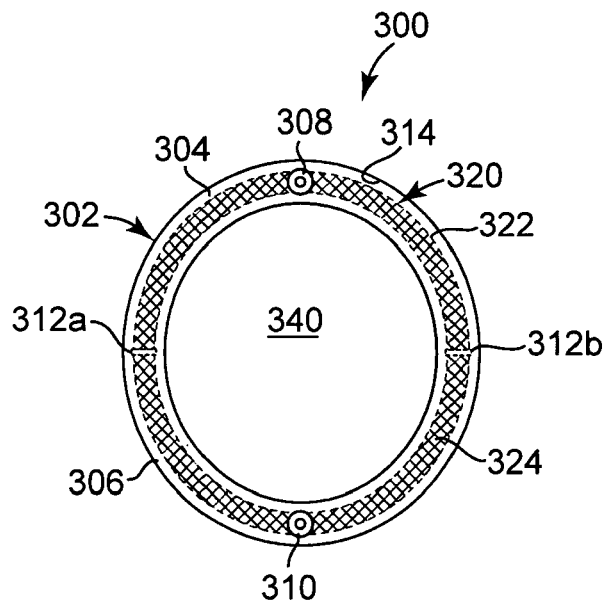
FIG. 9A is a plan view of a proximal side of a speculum frame including a flexible tubular frame and a coiled spring enclosed in the tubular frame according to another embodiment.
Figure 9B:
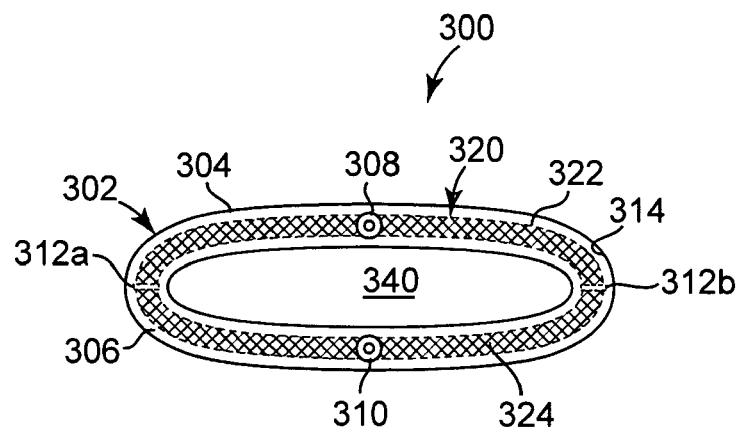
FIG. 9B is a plan view of the flexible tubular frame shown in FIG. 9A collapsed into an insertion state.

FIGS. 9A and 9B are plan views of a proximal side of a speculum 300 including a flexible frame 302 according to another embodiment. Speculum 300 includes speculum frame 302 having a first section 304 and a second section 306, a first handle assembly 308 coupled to first section 304, a second handle assembly 310 coupled to second section 306, a first hinge assembly 312a coupled between opposing ends of first and second section 304, 306, and a second hinge assembly 312b coupled between a second set of opposing ends of first and second sections 304, 306.

In one embodiment, frame 302 includes a flexible rubber housing 314 disposed over an exterior surface of a coiled spring 320. In one embodiment, coiled spring 320 includes a first coiled spring 322 extending through first section 304 between hinge assemblies 312a, 312b, and a second spring 324 extending through second section 306 between hinge assemblies 312a, 312b. In another embodiment, springs 322 and 324 combine to define a single continuous coiled spring 320 extending within a periphery of flexible housing 314, and separate hinge assembly lines 312a, 312b are formed in flexible housing 314 to define a part line for frame 302.

Housing 314 is flexible to enable first section 304 to collapse toward second section 306. In one embodiment, housing 314 is formed of a polymer tubing and frame 302 flattens when collapsed and forces hinge assembly 312a to the left, for example, and hinge assembly 312b to the right away from first hinge assembly 312a (as oriented in FIG. 9A and shown in FIG. 9B).

Figure 9C:
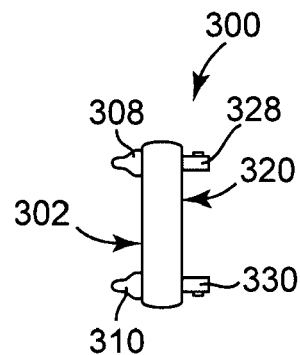
FIG. 9C is a side view of the collapsed flexible tubular frame shown in FIG. 9B illustrating a pair of opposing handle assemblies.

The view illustrated in FIGS. 9A and 9B is oriented toward the proximal side of speculum 300. FIG. 9C is a side view of speculum 300 showing blade portions 328, 330, respectively, extending from handle assemblies 308, 310. For clarity, the detachable mechanisms are omitted from the drawings. The blade portions 328, 330 are each configured to receive a speculum blade 24 (FIG. 2), and are each configured to independently move distal end portions of the attached blade 24 in a manner that is similar to the function of handle assemblies 212, 214 (FIG. 8).

When flexible housing 314 is collapsed, spring 320 flexes to enable frame 302 to flatten, reducing opening 340, and configure blades 24 for insertion into the patient during the gynecological procedure, and this orientation is illustrated in FIG. 9B. Spring 320 and hinge assemblies 312a, 312b configure speculum 300 to expand and recover to a substantially circular shape providing an expanded opening 340 (FIG. 9A).

Suitable springs 320 include coiled springs available from MW Industries, Logansport, Ind. Other suitable springs, such as torsion springs, compression springs, conical springs, are also acceptable.

Figure 10A:
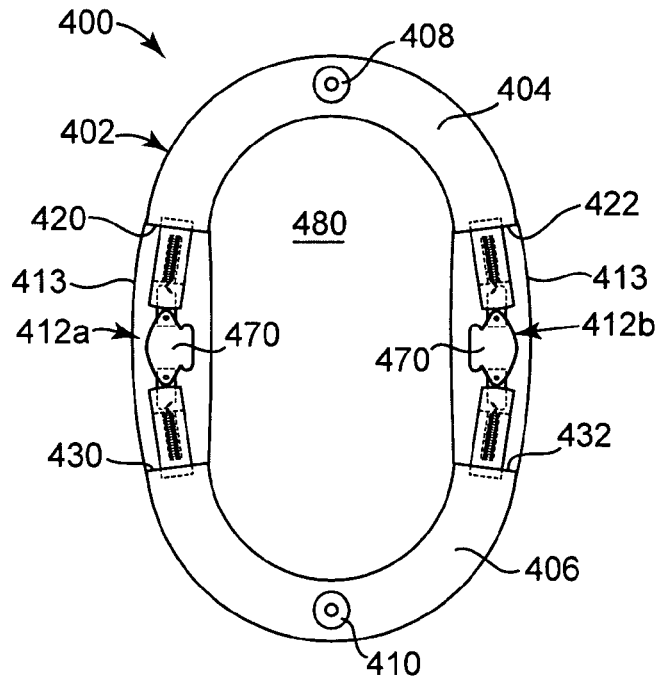
FIG. 10A is a plan view of a proximal side of a speculum frame including a pair of spring-loaded clip hinge assemblies each coupled between opposing arcuate segments of the speculum frame according to another embodiment.

FIG. 10A is a plan view of a proximal side of a vaginal speculum 400 according to another embodiment. Speculum 400 includes a frame 402 having a first section 404, a second section 406, a first handle assembly 408 coupled to first section 404, a second handle assembly 410 coupled to second section 406, and hinge assemblies 412a, 412b coupled between first section 404 and second section 406. A flexible sheath 413 is provided to protectively enclose hinge assemblies 412a, 412b, where the flexible sheath 413 flexes and moves as hinge assemblies 412a, 412b adjust a shape of frame 402. In one embodiment, flexible sheath is formed of an autoclavable silicone, although other suitable flexible materials are also acceptable. Hinge assemblies 412a, 412b include spring-loaded clips that flex laterally when a thumb piece 470 is deployed by the clinician to selectively collapse/expand first section 404 relative to second section 406.

In one embodiment, first section 404 includes a first end 420 spaced from a second end 422, and second section 406 includes a first end 430 spaced from a separate second end 432. First hinge assembly 412a is coupled between first ends 420, 430 of sections 404, 406, respectively, and second hinge assembly 412b is coupled between second ends 422, 432 of first and second sections 404, 406, respectively.

Figure 10B:
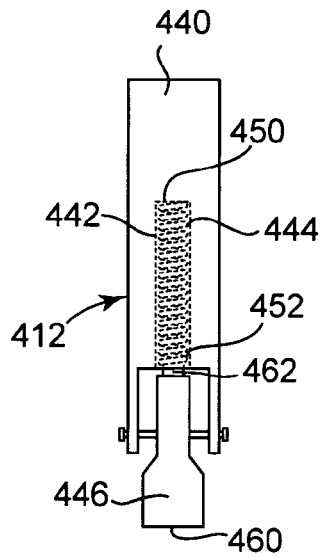
FIG. 10B is a side view and FIGS. 10C-10D are front views of one spring-loaded clip hinge assembly shown in FIG. 10A.
Figure 10C:
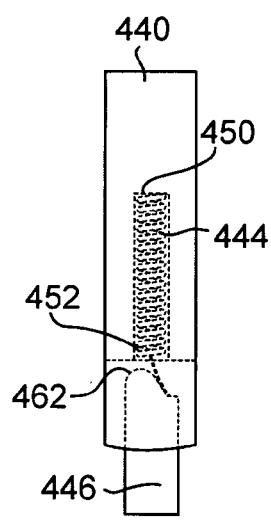
Figure 10D:
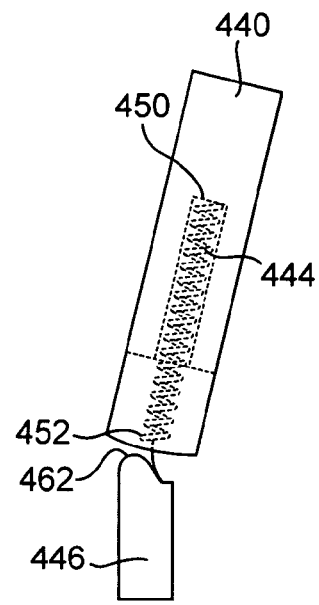

FIG. 10B is a side view and FIGS. 10C-10D are front views of hinge assembly 412a. With reference to FIG. 10B, in one embodiment hinge assembly 412a includes a base 440 defining a passage 442, a spring 444 insertable into passage 442, and a follower 446 coupled to spring 444. In general, base 440 is coupled to one of the ends 420, 430 of frame 402. In one embodiment, spring 444 is a compressed coil spring including a first end 450 coupled to a base of passage 442 and a second end 452 coupled to follower 446. In one embodiment, follower 446 includes a first end 460 configured to couple with thumb piece 470 (FIG. 10A) and a second end 462 coupled to spring 444. Hinge assembly 412a is configured to move between a substantially rigid state in which spring 444 and second end 462 of follower 446 are stowed in passage 442, and a flexed/open state in which follower 446 and spring 444 extend/expand out of passage 442. In this regard, hinge assembly 412 is similar to a climber's carabiner that is deployable between a fixed/clipped state and an open state.

Speculum 400 includes a first collapsed insertion state in which hinge assembly 412 collapses frame 402 and blades 24 contact (or nearly contact) one another, and a second deployed state in which hinge assembly 412 expands frame 402 and blades 24 are spread apart. In the first collapsed insertion state, follower 446 and spring 444 extend/expand out of passage 442 to enable first section 404 to bend/collapse toward second section 406. In the second deployed state, follower 446 and spring 444 are stowed in passage 442 and hinge assembly 412 supports first section 404 apart from second section 406. To this end, follower 446 is compressible into passage 442 to expand the periphery of frame 402. In the deployed state, sections 404, 406 are aligned in a planar fashion (shown in FIG. 10B) to provide a substantially circular periphery of frame 402 and define an opening 480 in speculum 400 (shown in FIG. 10A).

Figure 11A:
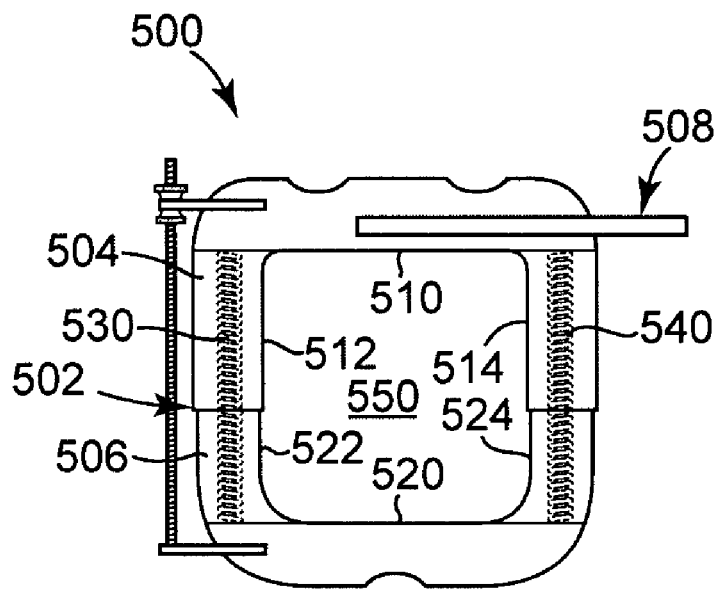
FIG. 11A is a plan view of a proximal side of a speculum frame including a rigid tubular frame housing a pair of opposing frame springs according to another embodiment.

FIG. 11A is a plan view of a proximal side of a vaginal speculum 500 according to another embodiment. Speculum 500 includes a substantially rigid frame 502 that is compressible up/down as oriented in FIG. 11A. Frame 502 includes a first section 504, a second section 506 insertable into a portion of first section 504, and a handle assembly 508 coupled to first section 504. In one embodiment, first section 504 defines a generally U-shaped section including a base 510, a first leg 512 extending from base 510, and a second leg 514 extending from base 510 and spaced apart from first leg 512. In one embodiment, second section 506 is also a generally U-shaped section including a base 520, a first leg extending from base 520, and a second leg 524 extending from base 520 and separated from first leg 522. In general, legs 512, 514 of first section 504 are tubular legs configured to receive tubular legs 522, 524 of second section 506, with a first spring 530 is disposed within tubular legs 512, 522, and a second spring 540 is disposed within tubular legs 514, 524. Springs 530, 540 bias sections 504, 506 away from each other and enable rigid frame 502 to collapse for insertion during a gynecological procedure.

When speculum 500 is so assembled, first section 504 is spring-loaded relative to second section 506, and a compressive force applied to first section 504 will compress first section 504 toward second section 506 by compressing springs 530, 540. In this manner, speculum 500 is configured to be compressed to a minimum size suitable for insertion of blades (not shown) into a vaginal introitus during a gynecological examination. After insertion, springs 530, 540 provide a recovery force that pushes first section 504 away from second section 506 to define an opening 550 within frame 502 of speculum 500. A frame retention mechanism 580, similar to frame retention mechanism 110 (FIG. 3), is provided to maintain a selected distance between biased portions 510, 520 of first section 504 and second section 506.

Figure 11B:
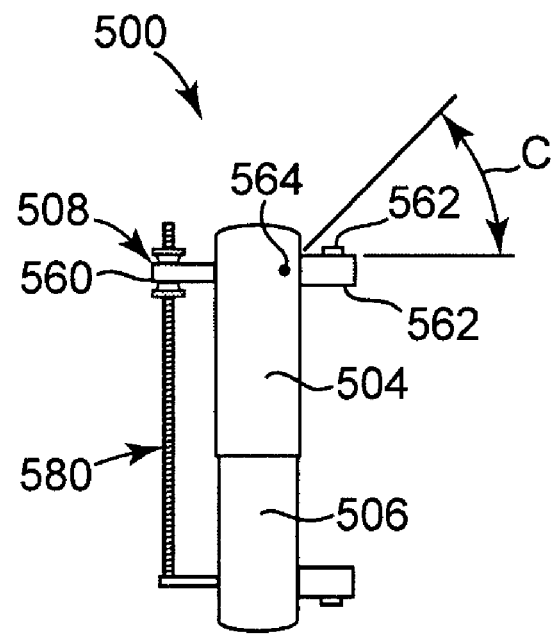
FIG. 11B is a side view of the speculum frame shown in FIG. 11A.

FIG. 11B is a side view of speculum 500. In one embodiment, handle assembly 508 includes a lever portion 560 and a blade portion 562, where handle assembly 508 is pivotally mounted to first section 504 about an axis 564. In general, movement of lever portion 560 downward translates to an upward movement of blade portion 562. In one embodiment, blade portion 562 is movable through a range from a substantially horizontal position to an angle C of about 45 degrees from the horizontal position. In this manner, movement or toggling lever portion 560 downward translates to an upward movement of blade portion 562 in the range of up to about 45 degrees. Lever portion 560 is similar to lever portions described above, and blade portion 562 is similar to the blade portions described above. In particular, blade portion 562 is configured to removably receive in socket-like fashion speculum blade 24 (FIG. 2).

Figure 12A:
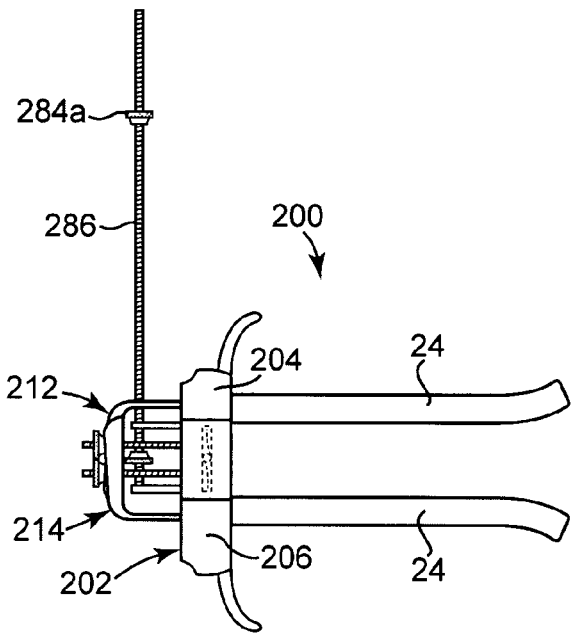
FIGS. 12A-12C are side views of the speculum shown in FIG. 8 illustrating a first collapsed insertion state and a second expanded deployed state according to one embodiment.
Figure 12B:
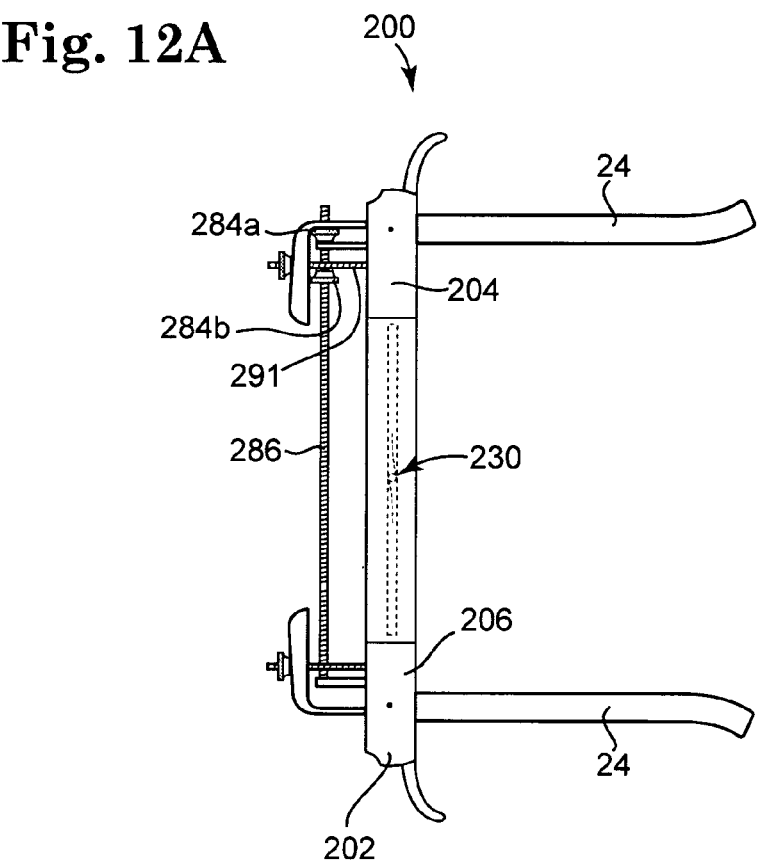
Figure 12C:
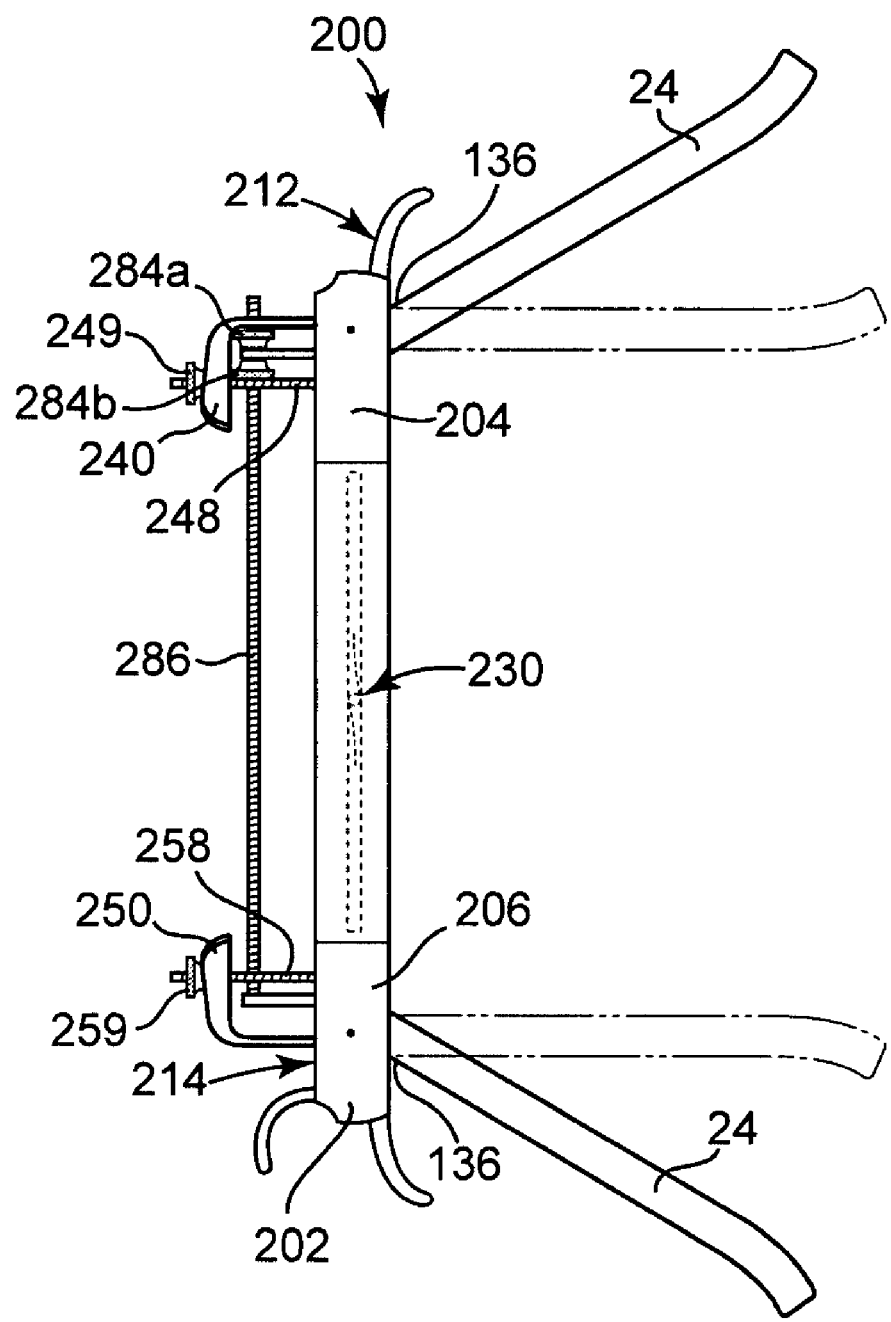

Operation of speculum 200 and blades 24 is described with reference to FIGS. 12A-12C. FIGS. 12A-12C are side views of the speculum shown in FIG. 8 illustrating a first collapsed insertion state (FIG. 12A) and a second expanded deployed state (FIGS. 12B-12C) according to one embodiment. Referring to FIGS. 8A and 12A, during a gynecological procedure, the clinician compresses first section 204 toward second section 206 to collapse blades 24 together into a first collapsed insertion state. It is to be understood that blades 24 are configured to be collapsed together and contact one another, but for ease of illustration blades 24 are shown spaced slightly apart to better show the relationship between first and second sections 204, 206. When collapsed, guide rod 286 extends upward beyond first section 204 and blades 24 touch (or nearly touch) and are suited for insertion into the vaginal introitus to assist in the gynecological procedure.

FIG. 12B is a side view of speculum 200 showing hinge assembly 230 expanding first section 204 apart from second section 206 such that speculum 200 occupies a deployed state in which an opening (not visible) is formed between first and second sections 204, 206. Blades 24 are positioned within the vaginal vault to support and part apposed walls of the vagina to provide access to an exterior wall of the cervix. In one embodiment, a cinch device in the form of nuts 284a, 284b is provided. Other forms of cinch device 284a, 284b are also acceptable. Nuts 284a, 284b are threaded along guide rod 286 until fastened against an upper flange 291 to selectively maintain sections 204, 206 in a desired deployed position. In general, nut 284a limits expansion of frame 202 and nut 284b provides a "stop" that limits collapse of frame 202 during a procedure.

FIG. 12C is a side view of speculum 200 in the second deployed state after lever portions 240, 250 have been moved to selectively diverge distal end portions of speculum blades 24. The clinician manipulates lever portions 240, 250 to diverge the distal end portions of speculum blades 24. In one embodiment, speculum blades 24 pivot and diverge up to about 45 degrees from the horizontal. When speculum blades 24 are positioned in the desired location, locks 249, 259 are secured against lever portion 240, 250, respectively, to lock handle assemblies 212, 214 in the desired deployed position. In one embodiment, movement of first lever portion 240 moves the distal end portion of first blade 24 apart, and movement of second lever portion 250 independently moves the other distal end portion of second blade 24 apart to diverge and support apposed walls of the vagina without increasing a distance between proximal ends 136 of blades 24. In one contrasting embodiment, when blades 24 are coupled to vaginal speculum assembly 20 illustrated in FIG. 2, the lower blade 24 does not move relative to frame 30. Upper blade 24 (FIG. 2) moves in response to movement of handle assembly 40.

Figure 13A:
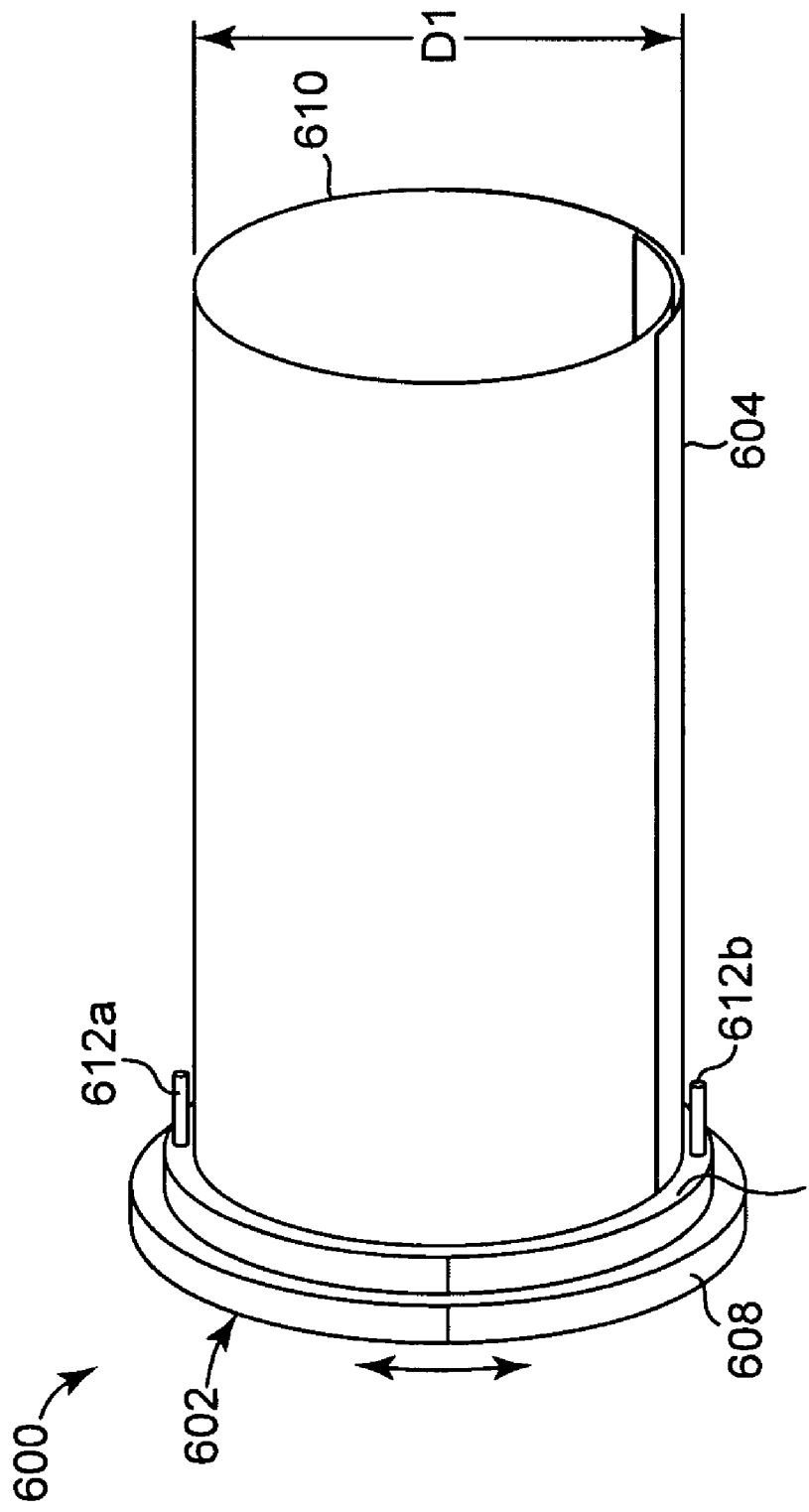
FIGS. 13A-B are perspective views of a lateral dilator according to another embodiment of the present disclosure.
Figure 13B:
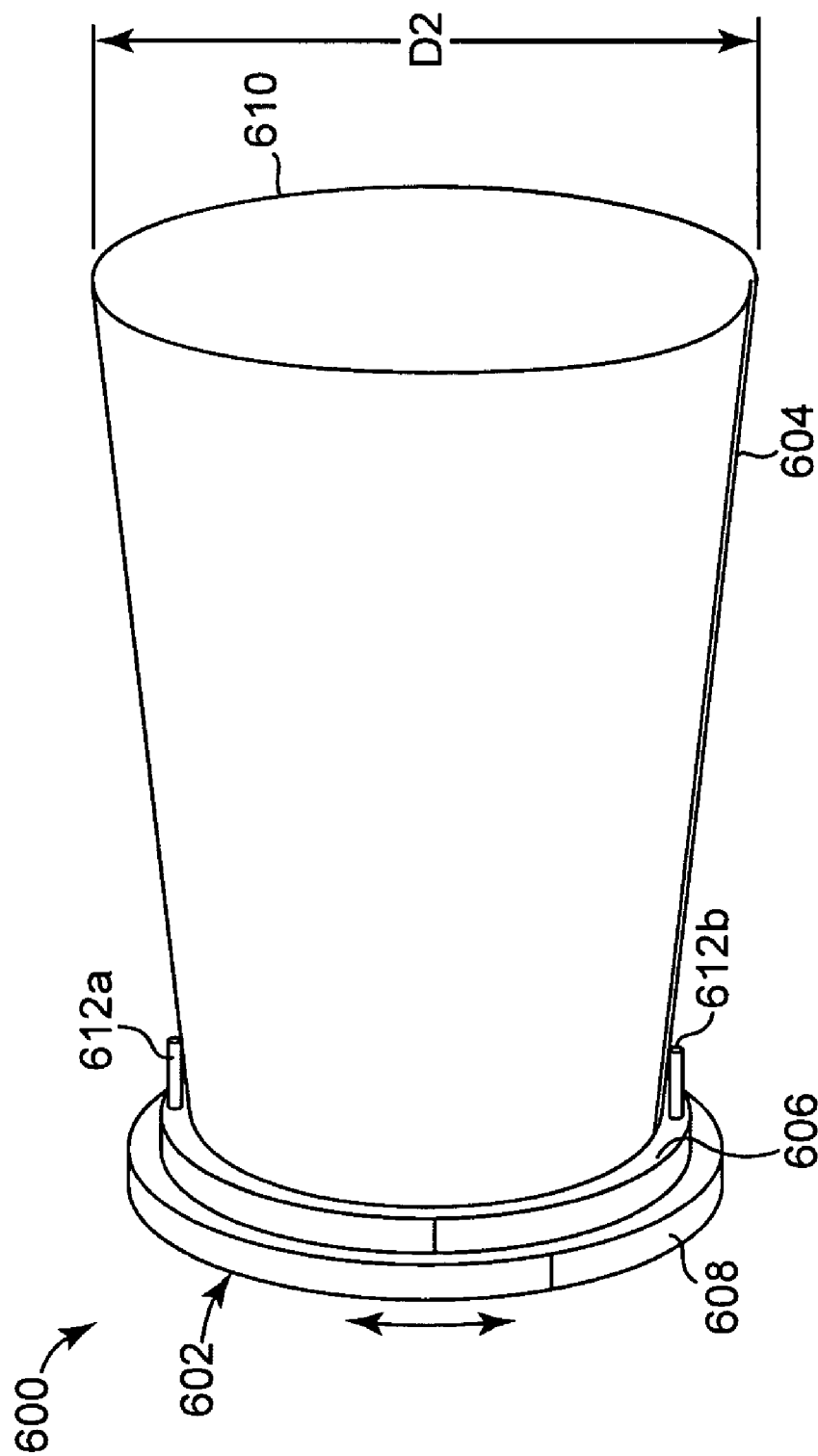

FIGS. 13A and 13B are perspective views of a lateral dilator 600 according to another embodiment. Dilator 600 is configured to couple to the speculum frames described above and includes a dilator handle assembly 602 and a blade assembly 604 coupled to dilator handle assembly 602. In one embodiment, dilator handle assembly 602 includes a first collar 606 and a second collar 608 that is rotatably coupled to first collar 606. Dilator 600 is configured such that movement of collar 608 relative to collar 606 selectively expands and contracts a distal end 610 of blade assembly 604. For example, FIG. 13A illustrates collar 608 in neutral alignment with collar 606 and distal end 610 of blade assembly 604 in a neutral state having a diameter D1, such that dilator 600 is configured for insertion into the opening of the above-referenced speculum frames. FIG. 13B illustrates collar 608 rotated relative to collar 606 such that distal end 610 is expanded to a diameter D2 that is greater than diameter D1.

In one embodiment, collar 606 includes pins 612a, 612b that are configured to coupled collar 606 to a frame of speculum 22, speculum 200, speculum 300, speculum 400, or speculum 500 described above. Other mechanisms configured for coupling collar 606 to a frame of a speculum are also acceptable.

In one embodiment, blade assembly 604 includes a sheet of material wrapped in cylindrical form and coupled to dilator handle assembly 602. In one embodiment, blade assembly 604 is formed from transparent material configured to transmit light. For example, lighted speculums are known in the art that accommodate a light that is useful in illuminating the speculum blades during a gynecological procedure. Dilator 600 is configured to be employed with these lighted speculums, and blade assembly 604 is formed of a transparent material that is configured to transmit the light emitted by the lighted speculum. In one embodiment, blade assembly 604 is fabricated from polyester, polyethylenenaphthlate, or other suitable polymer material, or one or more layers of these suitable polymer materials.

Figure 13C:
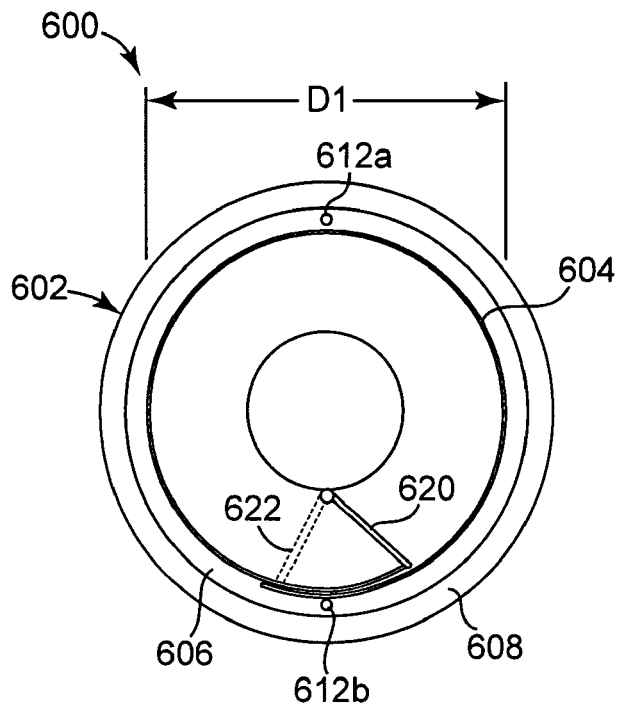
FIGS. 13C-D are front views of the lateral dilator shown in FIGS. 13A-B.
Figure 13D:
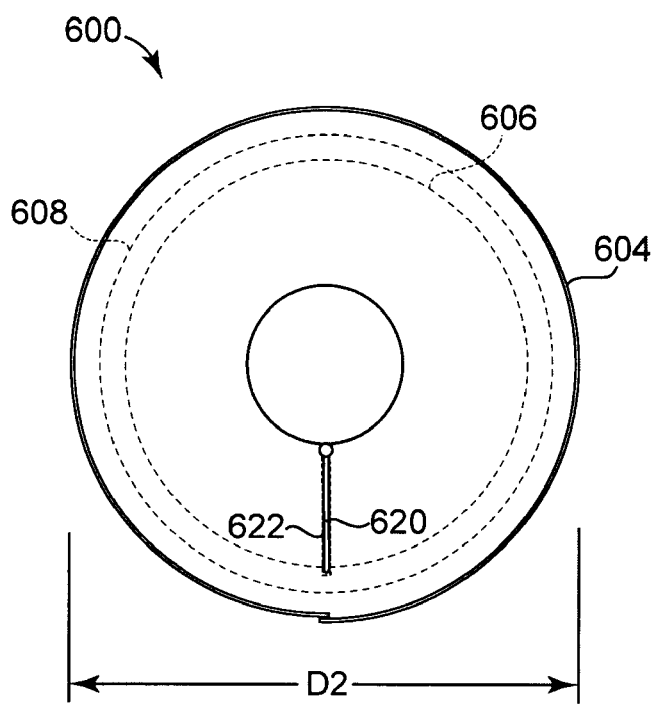

FIGS. 13C and 13D illustrate front views of dilator 600. In one embodiment, dilator 600 includes a brace 620 coupled between dilator handle assembly 602 and distal end 610 of blade assembly 604, where brace 620 is configured to couple with a groove 622 formed in an interior surface of blade assembly 604. In one embodiment, movement of collar 608 (FIGS. 13A-13B) moves brace 620 within groove 622 and changes the diameter of distal end 610 of lateral dilator 600.

FIG. 13C illustrates brace 620 when distal end 610 of blade assembly 604 is in a first state having a diameter D1 that is suited for insertion into a frame of one of the speculums described above.

FIG. 13D illustrates distal end 610 of blade assembly 604 in an expanded state having diameter D2 that is larger than diameter D1, such that lateral dilator 600 is suited for providing an improved visualization pathway to the cervix during a gynecological procedure. In one embodiment, D2 is larger than D1, for example D2 is between about 1.25D1 to about 2.25D1, preferably D2 is about 1.5D1 such that D2 expands to about 50% larger than D1.

FIG. 14A is an exploded side view of an illuminated speculum 700 according to one embodiment. Speculum 700 includes a frame 702 including a first segment 704 and a second segment 706, a blade support 708 coupled to first segment 704 that is configured to receive a blade 710, and a blade support 712 coupled to second segment 706 that is configured to receive blade 714. In one embodiment, frame 702 is similar to frame 30 described above in FIG. 2 and includes a hinge assembly 720 configured to collapse first segment 704 toward second segment 706, a frame retention mechanism 722 configured to selectively maintain first segment 704 positioned relative to second segment 706, and a handle assembly 724 including a handle 726 that is coupled to blade support 708.

In one embodiment, blade support 708 includes a socket connector 730 that is configured to couple with socket 732 of blade 710 to removably retain blade 710 relative to frame 702, and blade support 712 includes a socket connector 740 that is configured to couple with socket 742 of blade 714 to removably retain blade 714 on blade support 712. In one embodiment, blade support 712 and socket connector 740 are configured such that a light source is activated when blade 714 is coupled to support 712, as described below.

In one embodiment, blade support 708 is movable and blade support 712 is fixed. For example, in one embodiment movement of handle 726 moves blade support 708 up and down relative to the orientation of FIG. 14 such that blade 710, when coupled to blade support 708, likewise moves up and down. The selective movement of blade 710 contributes to improved access and visualization of the cervical area during a gynecological procedure.

FIG. 14B is a side view of an illuminated blade support 712. In one embodiment, blade support 712 is fixed relative to frame 702 and includes an illumination assembly 750 including a light source 752 and an energy source 754. In one embodiment, illumination assembly 750 is disposed adjacent to a distal end portion 756 of blade support 712 such that speculum 700 is weight-biased to provide a weight forward speculum 700. In one embodiment, energy source 754 is provided separately from blade support 712, for example within frame 702 (FIG. 14A), or alternatively, exterior to speculum 700. Illumination assembly 750 is contained within blade support 712. When blade 714 is engaged over blade support 712, illumination assembly 750 is protected from possible cross-contamination associated with the use of speculum 700 in a clinical setting having multiple patients/procedures. In one embodiment, blade 714 is a single use blade and light source 752 is reusable. In combination, disposable blade 714 is configured to minimize the potential for undesirable cross-contamination of reusable light source 752 when speculum 700 is employed with more than one patient.

In one embodiment, light source 752 is a light-emitting diode and energy source 754 is a battery. Other forms of light source 752 and energy source 754 are also acceptable, including Xenon or incandescent bulbs and lithium ion batteries. In one embodiment, illumination assembly 750 is removably coupled to blade support 712, for example by a threaded attachment represented by line 760. In one embodiment, illumination assembly 750 is integrally formed in distal end portion 756 of blade support 712. In one embodiment, illumination assembly 750 is provided apart from blade support 712 and light is delivered to distal end portion 756 by fiber optic means such as fiber optic stands and/or cables. For example, in one embodiment light source 752 is disposed on frame 702 and light is transmitted along blade support 712 via a fiber optic component.

In one embodiment, blade 714 is configured to enable light generated by light source 752 to transmit through at least a portion of blade 714. For example, in one embodiment at least one surface 770 of blade 714 is fabricated of transparent material and is configured to enable light to shine on the region between blades 710, 714. Suitable transparent materials for surface 770 include silicones, such as clear silicones, polyacrylates, methacrylates, polycarbonates, blends and co-polymers of these materials and other optically clear polymeric materials.

FIGS. 14A and 14B provides one exemplary embodiment of an expandable and collapsible vaginal speculum frame including a weight forward illumination assembly. During use, blades 710, 714 are coupled to respective blade supports 708, 712 and speculum 700 is inserted into the vaginal introitus as described above. Illumination assembly 750 is activated to provide light 772 that emanates from light source 752 through surface 770 of blade 714. In this manner, speculum 700 provides improved illumination of the cervical region, even in patients having a prolapsed vaginal vault or in bariatric patients.

Figure 15:
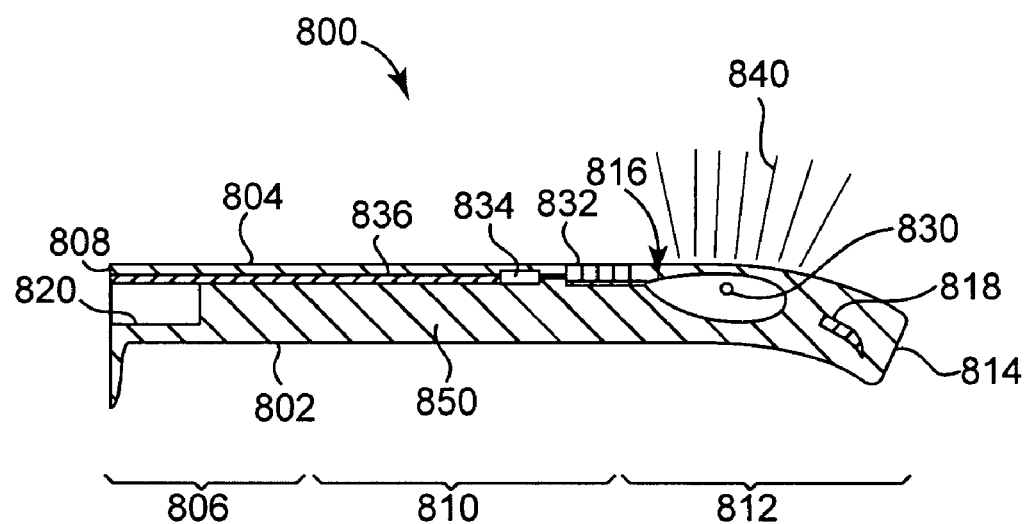
FIG. 15 is a cross-sectional view of a speculum blade attachable to a speculum frame, where the speculum blade is distally weighted and includes an illumination assembly according to one embodiment.

FIG. 15 is a cross-sectional view of an illuminated speculum blade 800 according to one embodiment. Illuminated speculum blade 800 includes an exterior surface 802 configured for patient contact opposite an interior surface 804, a proximal end portion 806 extending between a proximal end 808 and a central portion 810, a distal end portion 812 extending between a distal end 814 and central portion 810, and an illumination assembly 816. In one embodiment, illuminated speculum blade 800 is configured to provide a speculum to which it is attached with a forward-biased weight distribution. To this end, one embodiment of blade 800 optionally includes an additional weight 818 disposed in proximal end portion 812.

In one embodiment, proximal end 808 defines a socket 820 that is configured to couple with a blade portion of a speculum frame, such as blade portion 52 described above in FIG. 2.

In one embodiment, illumination assembly 816 includes a light source 830, an energy source 832, and control circuitry 834 disposed within speculum blade 800. In one embodiment, illumination assembly 816 optionally includes wiring 836 extending from light source 830 to proximal end 808 that is suited for coupling to an external power source. In one embodiment, illumination assembly 816 is provided apart from speculum blade 800 and configured to deliver light to distal end portion 812, which is configured to permit the light to pass therethrough. In one embodiment, light source 830 and/or energy source 832 is/are provided separately from speculum blade 800, for example within the speculum frame to which blade 800 attaches, or alternatively, exterior to the speculum frame.

In one embodiment, light source 830 includes a light-emitting diode, energy source 832 includes one or more batteries, and control circuitry 834 is configured to selectively activate light source 830 between on and off positions. In one embodiment, control circuitry 832 is configured to sense when blade portion 52 (FIG. 2) is inserted into socket 820, subsequently illuminating light source 830 when blade 800 is assembled to speculum frame 30, for example.

In one embodiment, interior surface 804 is formed of a transparent material and configured to enable light 840 emitted from light source 830 to be transmitted through interior surface 804. In one embodiment, a body portion 850 of blade 800 includes a transparent polymeric material that is molded around illumination assembly 816 and configured to enable the passage of light. Suitable transparent materials for body portion 850 include silicones, such as clear silicones, polyacrylates, methacrylates, polycarbonates, blends and co-polymers of these materials and other optically clear polymeric materials.

FIG. 15 provides an exemplary embodiment of an illuminated speculum blade that is configured to be removably attached to a speculum frame. The illuminated speculum blade provides illumination adjacent to a distal end portion of the blade (and thus the speculum), which provides light for improved illumination of the cervical region, even in patients having a prolapsed vaginal vault or in bariatric patients.

Figure 16A:
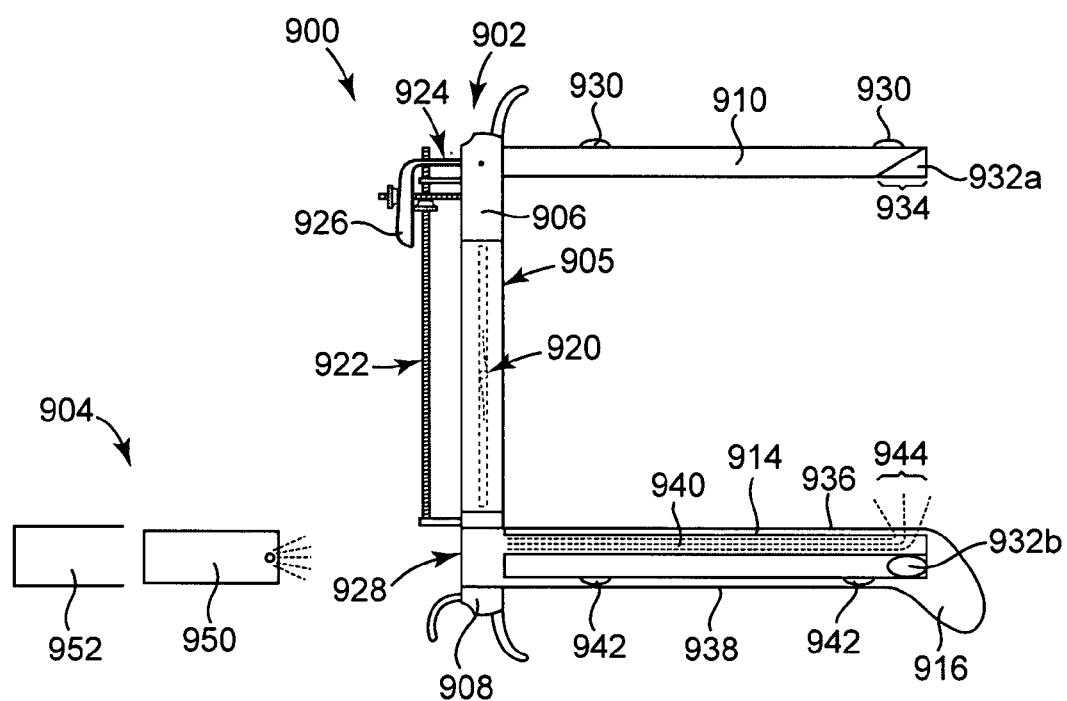
FIG. 16A is an exploded side view of an illuminated speculum assembly including a speculum and a light assembly configured to couple with the speculum according to another embodiment.

FIG. 16A is an exploded side view of an illuminated speculum assembly 900 according to another embodiment. Speculum assembly 900 includes a speculum 902 and a removable light assembly 904 that is insertable into speculum 902. Illuminated speculum assembly 900 is configured to provide improved visualization of the vaginal vault in the region of the cervix through a light source that is suited for repeated use while minimizing the potential for cross-contamination between patients.

In one embodiment, speculum 902 includes a frame 905 including a first segment 906 and a second segment 908, a blade support 910 coupled to first segment 906 that is configured to receive a blade similar to blade 710 (FIG. 14A), and a blade support 914 coupled to second segment 908 that is shown coupled to a blade 916.

In one embodiment, frame 905 is similar to frame 30 (FIG. 2) and includes a hinge assembly 920 configured to collapse first segment 906 toward second segment 908, a frame retention mechanism 922 configured to selectively maintain first segment 906 relative to second segment 908, a handle assembly 924 including a handle 926 that is coupled to blade support 910, and a passageway 928 that communicates with blades support 914.

In one embodiment, blade support 910 includes connectors 930 and a weight 932a. Connectors 930 are configured to couple into a socket similar to the socket 732 defined by blade 710 (FIG. 14A) to removably retain the blade relative to frame 905. Weight 932a is disposed at a distal end portion 934 of blade support 910, and thus configured to provide speculum 902 with a weight-forward construction that resists sliding or displacement when inserted into the vaginal vault.

In one embodiment, weight 932a is a solid mass of metal configured to transfer a balance point of speculum 902 toward its distal end portion. In one embodiment, blade support 914 defines a light pipe 940, a weight 932b similar to weight 932a, and connectors 942 that are configured to couple with and removably retain blade 916. In one embodiment, light pipe 940 defines a hollow segment that is configured to transmit light from light assembly 904 toward distal end portion 944 of blade support 914. In one embodiment, the hollow segment defined by light pipe 940 includes a surface that is configured to enable light to pass along its length. Suitable material for forming light pipe 940 includes, mirrored surfaces or optical film such as 3M brand Optical Lighting Film, available from 3M Company, St. Paul, Minn. In one embodiment, blade 916 is a single-use disposable blade that is configured to transmit light through at least a distal end portion 944 of blade support 914. For example, in one embodiment blade 916 includes an optically clear side 936 and an optically opaque side 938. Optically clear side 936 is generally provided on the side of blade 916 that is oriented towards the vaginal vault/cervix, and opaque side 938 is generally oriented toward the vaginal wall. In this manner, light emitted from light assembly 904 is incident upon the cervix.

In one embodiment, light assembly 904 includes a light source 950 and a cover 952. In one embodiment, light source 950 is a self-contained light emitting diode (LED) light source that is activated (e.g., "turned on") and inserted into passageway 928 defined by frame 905. Light source 950 includes the LED and an energy source for powering the LED and is configured to emit light that travels along light pipe 940 toward distal end portion 944 of blade support 914. In one embodiment, light is selective emitted from one side of distal end portion 944, for example the side oriented in the direction between blade supports 910, 914. In another embodiment, light is emitted radially from distal end portion 944 of blade support 914.

In another embodiment, light source 950 is inserted into passageway 928 and covered by cover 952, and light source 950 illuminates in response to blade 916 coupling with blade support 914.

Figure 16B:
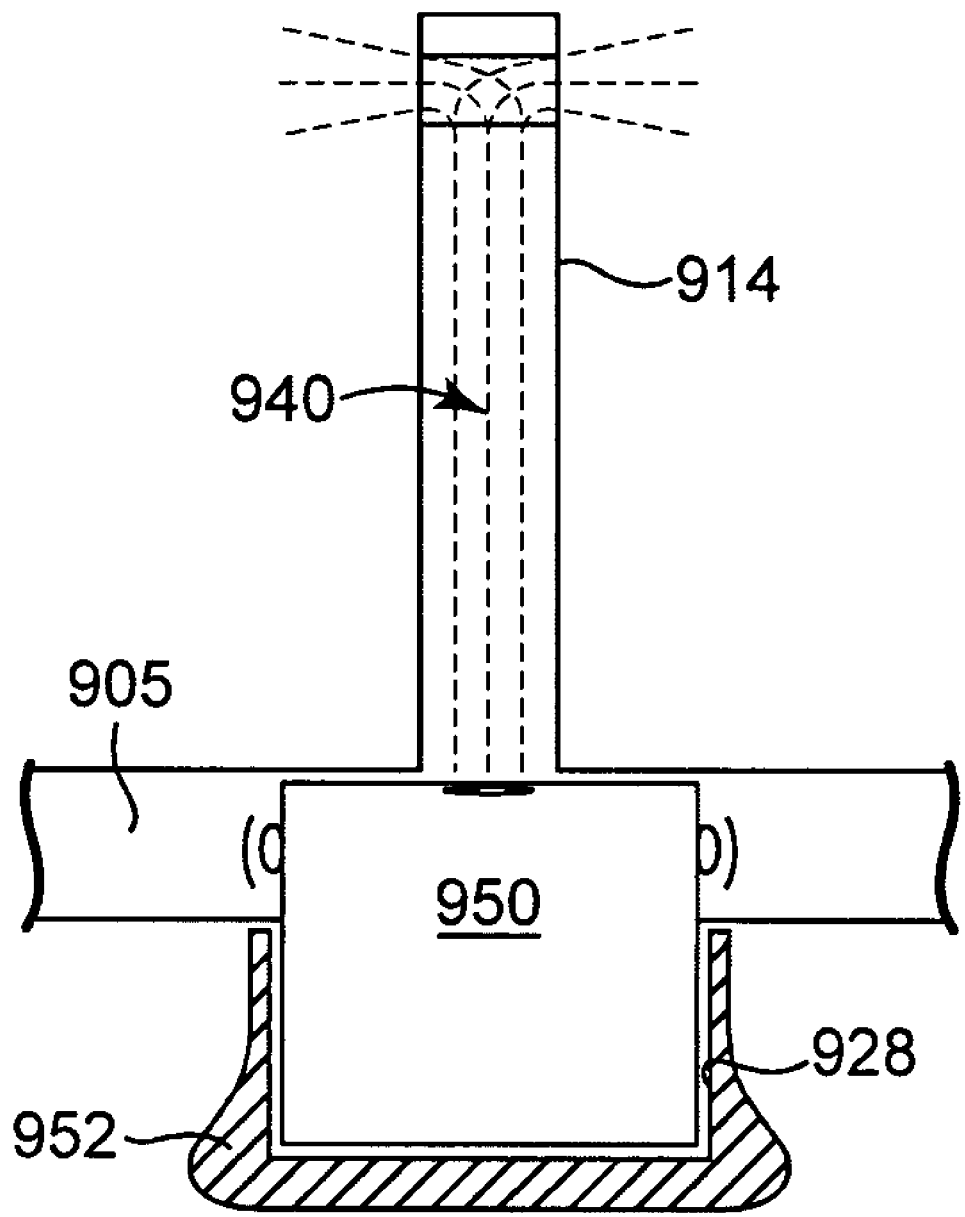
FIG. 16B is a top view of the illuminated speculum assembly shown in FIG. 16A illustrating the light assembly inserted into a frame of the speculum.

FIG. 16B is a top view of the illuminated speculum assembly 900 shown in FIG. 16A illustrating light source 950 inserted into frame 905 of speculum 902. Cover 952 is provided to minimize contamination of light source 952 during a gynecological examination. In one embodiment, cover 952 is a rigid cover that provides a housing for light source 950 and a handle configured to assist in manipulating light source 950. One exemplary embodiment of cover 952 is configured to activate light source 950 when cover 952 is snapped or positioned over light source 950 and/or coupled to frame 905. Suitable materials for forming cover 952 include polymer materials, such as polyethylene or other polyolefins, polyester, or nylon.

In another embodiment, cover 952 is a thin-film aseptic drape configured to provide a clean and/or aseptic field over light source 950. In general, cover 952 is configured to minimize the potential for contamination and cross-contamination of the reusable light source 950 during gynecological procedures. In one embodiment, cover 952 includes a thin-film formed as a plastic drape having a thickness of between about 0.0005 to 0.050 inches having adhesive applied to one surface that is configured to attach drape/cover 952 to light source 950. Suitable materials for drape/cover 952 include plastic films in general and polyethylene films and block co-polymer films in particular.

During use, and with reference to FIGS. 16A-16B, blade 916 is coupled to blade support 914 and light source 950 is inserted into passageway 928. Light source 950 is either activated prior to insertion into passageway 928, or light source 950 is activated when cover 952 is placed over light source 950 and coupled to frame 905. Light from light source 950 travels along light pipe 940 defined by blade support 914, passes through optically clear side 936 of blade 916, and is incident on the cervix. Cover 952 prevents or minimizes the possibility of contamination of light source 950 by biological material. Light source 950 and frame 905 are reusable, and cover 952 and blade 916 are disposable to provide an illuminated speculum assembly 900 that provides improved visualization of the vaginal vault and cervix while minimizing the potential for cross-contamination of biological material between patients.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A vaginal speculum comprising:
    a frame that defines a proximal side and a distal side and an opening within the frame between a first blade that is attachable to the frame and a second blade that is attachable to the frame opposite of the first blade, the frame including a hinge assembly configured to flex the frame to selectively change a size of the opening; and
    a first handle assembly including a lever portion and a blade portion coupled to the lever portion, the first handle assembly pivotally mounted to the frame such that the lever portion extends from the proximal side of the frame and the blade portion extends from the distal side of the frame, each of the opposing first and second blades having a proximal end configured for attachment to the blade portion of the handle assembly and a distal end portion spaced from the proximal end;
    wherein in a first collapsed insertion state the hinge assembly collapses the frame and the first blade contacts the second blade, and in a second deployed state the hinge assembly expands the frame and the first blade is spaced apart from the second blade; and
    wherein the blade portion of the first handle assembly comprises a socket head that is configured to releasably couple with a socket formed in the proximal end of the first blade.

2. The vaginal speculum of claim 1, wherein the frame comprises:
    a first arcuate segment including a first end and a separate second end, the first blade attachable to the first arcuate segment;
    a second arcuate segment including a first end and a separate second end, the second blade attachable to the second arcuate segment;
    a first hinge coupled between the first ends of the first and second arcuate segments; and
    a second hinge coupled between the second ends of the first and second arcuate segments.

3. The vaginal speculum of claim 2, wherein the first and second arcuate segments each comprise:
    a flexible tubular housing; and
    a coiled spring disposed within the housing, the coiled spring extending between the first and second ends of a respective one of the arcuate segments.

4. The vaginal speculum of claim 3, wherein each of the first and second hinges include a spring-loaded clip comprising:
    a base defining a slot, a spring inserted into the slot, and a follower including first and second opposing ends, the first end of the follower coupled to the spring and configured to slide into the slot;
    wherein the base is coupled to one of the first and second arcuate segments, and the second end of the follower is coupled to an other of the first and second arcuate segments, such that the follower is compressible into the slot of the base when the frame is in the second deployed state.

5. The vaginal speculum of claim 2, wherein the first and second arcuate segments each comprise:
a rigid housing including a base, a first tubular leg extending from the base, and a second tubular leg extending from the base separated from the first tubular leg; and
a first coiled spring disposed within one of the first tubular legs and a second coiled spring disposed within one of the second tubular legs;
wherein the first hinge comprises the first tubular leg of the first arcuate segment inserted within the first tubular leg of the second arcuate segment in a manner that contains the first coiled spring, and the second hinge comprises the second tubular leg of the first arcuate segment is insertable within the second tubular leg of the second arcuate segment in a manner that contains the second coiled spring.

6. The vaginal speculum of claim 2, wherein the first and second arcuate segments each comprise:
a rigid semi-circular housing;
wherein the first hinge comprises a leaf spring coupled between the first ends of the first and second arcuate segments, and the second hinge comprises a separate leaf spring coupled between the second ends of the first and second arcuate segments.

7. The vaginal speculum of claim 2, further comprising:
a frame retention mechanism including a first flange coupled to the first arcuate segment, a second flange coupled to the second arcuate segment, and means coupled between the first and second flanges to maintain the first arcuate segment in a position relative to the second arcuate segment.

8. The vaginal speculum of claim 1, further comprising:
a second handle assembly mounted to the frame opposite of the first handle assembly, the second handle assembly including a second lever portion and a second blade portion coupled to the second lever portion, the second lever portion extending away from the proximal side of the frame and the second blade portion extending from the distal side of the frame, the first blade removably attached to the first blade portion and the second blade removably attached to the second blade portion;
wherein when the opposing first and second blades are inserted into a vaginal introitus, movement of the first lever portion moves the distal end portion of the first blade apart from the distal end portion of the second blade to diverge and support apposed walls of the vagina without increasing a distance between the proximal ends of the opposing first and second blades.

9. The vaginal speculum of claim 8, wherein the second handle assembly is pivotally mounted to the frame and movement of the first and second lever portions moves a respective distal end portion of the opposing first and second blades one apart from an other to diverge and support apposed walls of the vagina without increasing a distance between the proximal ends of the opposing first and second blades.

10. The vaginal speculum of claim 1, further comprising:
at least one lip coupled to and extending from the distal side of the frame, the at least one lip configured to appose the patient when the opposing first and second blades are inserted into a vaginal canal.

11. The vaginal speculum of claim 1, further comprising:
a lateral dilator insertable into the opening, the lateral dilator comprising:

a collar including a collar wall configured to removably couple with the frame; and
at least one blade extending from the collar and including a dilator handle assembly mounted to the collar that is configured to move distal end portions of the lateral blades.

12. The vaginal speculum of claim 11, wherein the at least one blade extending from the collar is configured to transmit light therethrough.

13. A vaginal speculum assembly comprising:
a frame including:
a first segment including a first end and a separate second end, a second segment including a first end and a separate second end,
means coupled between respective first ends of the first and second segments and respective second ends of the first and second segments to flex the frame;
a first speculum blade attachable to the first segment and a second speculum blade attachable to the second segment;
a lateral dilator configured for insertion through an opening defined by the frame, the lateral dilator coupleable to the frame and including at least one blade having a distal end that is movable; and
wherein the means coupled between respective first ends of the first and second segments and respective second ends of the first and second segments to flex the frame comprises a first spring coupled between respective first ends of the first and second segments and a second spring coupled between respective second ends of the first and second segments.

14. A vaginal speculum comprising:
a frame that defines a proximal side and a distal side and an opening within the frame between a first blade that is attachable to the frame and a second blade that is attachable to the frame opposite of the first blade, the frame including a hinge assembly configured to flex the frame to selectively change a size of the opening; and
a first handle assembly including a lever portion and a blade portion coupled to the lever portion, the first handle assembly pivotally mounted to the frame such that the lever portion extends from the proximal side of the frame and the blade portion extends from the distal side of the frame, each of the opposing first and second blades having a proximal end configured for attachment to the blade portion of the handle assembly and a distal end portion spaced from the proximal end;
wherein in a first collapsed insertion state the hinge assembly collapses the frame and the first blade contacts the second blade, and in a second deployed state the hinge assembly expands the frame and the first blade is spaced apart from the second blade;
wherein the frame comprises: a first arcuate segment including a first end and a separate second end, the first blade attachable to the first arcuate segment; a second arcuate segment including a first end and a separate second end, the second blade attachable to the second arcuate segment; a first hinge coupled between the first ends of the first and second arcuate segments; and a second hinge coupled between the second ends of the first and second arcuate segments; and
wherein the first and second arcuate segments each comprise: a rigid semi-circular housing; wherein the first hinge comprises a leaf spring coupled between the first ends of the first and second arcuate segments, and the second hinge comprises a separate leaf spring coupled between the second ends of the first and second arcuate segments.

15. A vaginal speculum comprising:

a frame that defines a proximal side and a distal side and an opening within the frame between a first blade that is attachable to the frame and a second blade that is attachable to the frame opposite of the first blade, the frame including a hinge assembly configured to flex the frame to selectively change a size of the opening; and a first handle assembly including a lever portion and a blade portion coupled to the lever portion, the first handle assembly pivotally mounted to the frame such that the lever portion extends from the proximal side of the frame and the blade portion extends from the distal side of the frame, each of the opposing first and second blades having a proximal end configured for attachment to the blade portion of the handle assembly and a distal end portion spaced from the proximal end;

wherein in a first collapsed insertion state the hinge assembly collapses the frame and the first blade contacts the second blade, and in a second deployed state the hinge assembly expands the frame and the first blade is spaced apart from the second blade; and at least one lip coupled to and extending from the distal side of the frame, the at least one lip configured to appose the patient when the opposing first and second blades are inserted into a vaginal canal.

16. A vaginal speculum comprising:

a frame that defines a proximal side and a distal side and an opening within the frame between a first blade that is attachable to the frame and a second blade that is attachable to the frame opposite of the first blade, the frame including a hinge assembly configured to flex the frame to selectively change a size of the opening; and a first handle assembly including a lever portion and a blade portion coupled to the lever portion, the first handle assembly pivotally mounted to the frame such that the lever portion extends from the proximal side of the frame and the blade portion extends from the distal side of the frame, each of the opposing first and second blades having a proximal end configured for attachment to the blade portion of the handle assembly and a distal end portion spaced from the proximal end;

wherein in a first collapsed insertion state the hinge assembly collapses the frame and the first blade contacts the second blade, and in a second deployed state the hinge assembly expands the frame and the first blade is spaced apart from the second blade;

a lateral dilator insertable into the opening, the lateral dilator comprising:

a collar including a collar wall configured to removably couple with the frame; and at least one blade extending from the collar and including a dilator handle assembly mounted to the collar that is configured to move distal end portions of the lateral blades.

* * * * *